US009895467B2

(12) United States Patent
Grubbs et al.

(10) Patent No.: US 9,895,467 B2
(45) Date of Patent: Feb. 20, 2018

(54) LIGHT ADJUSTABLE INTRAOCULAR LENSES USING UPCONVERTING NANOPARTICLES AND NEAR INFRARED (NIR) LIGHT

(71) Applicant: CALIFORNIA INSTITUTE OF TECHNOLOGY, Pasadena, CA (US)

(72) Inventors: Robert H. Grubbs, South Pasadena, CA (US); Shane L. Mangold, Glendale, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/154,039

(22) Filed: May 13, 2016

(65) Prior Publication Data

US 2016/0331868 A1 Nov. 17, 2016

Related U.S. Application Data

(60) Provisional application No. 62/161,415, filed on May 14, 2015.

(51) Int. Cl.
| | |
|---|---|
| C08F 2/46 | (2006.01) |
| C08F 2/50 | (2006.01) |
| C08G 61/04 | (2006.01) |
| A61L 27/50 | (2006.01) |
| C08F 222/38 | (2006.01) |
| A61L 27/04 | (2006.01) |
| A61L 27/14 | (2006.01) |
| A61F 2/16 | (2006.01) |
| A61F 9/00 | (2006.01) |

(52) U.S. Cl.
CPC ............ *A61L 27/50* (2013.01); *A61F 2/1627* (2013.01); *A61F 2/1635* (2013.01); *A61F 2/1659* (2013.01); *A61F 9/00* (2013.01); *A61L 27/047* (2013.01); *A61L 27/14* (2013.01); *C08F 222/385* (2013.01); *A61L 2400/06* (2013.01); *A61L 2400/12* (2013.01); *A61L 2430/16* (2013.01)

(58) Field of Classification Search
CPC ...... A61L 27/50; A61L 27/16; A61L 2430/16; A61L 2400/06; A61L 27/14; A61L 2400/12; A61L 27/47; A61F 9/007; A61F 2/1659; A61F 2/1624; C08F 222/385
USPC ............... 522/48, 47, 6, 71, 189, 184; 520/1
See application file for complete search history.

(56) References Cited

U.S. PATENT DOCUMENTS

| | | | |
|---|---|---|---|
| 7,727,544 B2 | 6/2010 | Schwartz | |
| 8,414,911 B2 | 4/2013 | Mattson et al. | |
| 2005/0027031 A1 | 2/2005 | Chang et al. | |
| 2011/0171320 A1* | 7/2011 | Dantus ................. | A61K 9/0048 424/617 |
| 2012/0089180 A1* | 4/2012 | Fathi .................... | B41J 2/17559 606/214 |
| 2013/0278989 A1* | 10/2013 | Lam .......................... | B60J 3/04 359/275 |
| 2013/0323685 A1* | 12/2013 | Ostler .................... | A61K 6/083 433/228.1 |
| 2014/0148880 A1 | 5/2014 | Deisseroth et al. | |

OTHER PUBLICATIONS

Auzel, "Upconversion and Anti-Strokes Processes with f and d Ions in Solids", Chemical Reviews, 2004, 104, 139-173.
Boyer et al., "Synthesis of Colloidal Upconverting $NaYF_4$ Nanocrystals Doped with $Er^{3+}$, $Yb^{3+}$ and $Tm^{3+}$ via Thermal Decomposition of Lanthanide Trifluoroacetate Precursors", Journal of the American Chemical Society, May 2006, 128, 23, 7444-7445.
Bunzli et al., "Taking advantage of luminescent lanthanide ions", Chemical Society Reviews, Jun. 2005, 34, 1048-1077.
Haase et al., "Upconverting Nanoparticles", Angewandte Chemie International Edition, May 2011, 50, 5808-5829.
Jacques, "Corrigendum: Optical properties of biological tissues: a review", Physics in Medicine and Biology, Jun. 2013, 58, R37-R61.
Kramer et al., "Hexagon Sodium Yttrium Fluoride Based Green and Blue Emitting Upconversion Phosphors", Chemistry of Materials, 2004, 16, 1244-1251.
Li et al., "An efficient and user-friendly method for the synthesis of hexagonal-phase$NaYF_4$:Yb, Er/Tm nanocrystals with controllable shape and upconversion fluorescence", Nanotechnology, Jul. 2008, 19, 345606. 5 pages.
Li et al., "Lab on upconversion nanoparticles: optical properties and applications engineering via designed nanostructure", Chemical Society Reviews, 2015, 44, 1346-1378.
Resch-Genger et al., "Quantum dots versus organic dyes as fluorescent labels", Nature Methods, Aug. 2008, 5, 763-775.
Sedlmeier et al., "Surface modification and characterization of photon-upconverting nanoparticles for bioanalytical applications", Chemical Society Reviews, 2015, 44, 1526-1560.
Sun et al., "Upconversion of Rare Earth Nanomaterials", Annual Reviews Physical Chemistry, Feb. 2015, 66, 619-642.
Wang et al., "Upconversion nanoparticles in biological labeling, imaging, and therapy", Analyst, 2010, 135, 1839-1854.

(Continued)

*Primary Examiner* — Jessica Whiteley
(74) *Attorney, Agent, or Firm* — Baker & Hostetler LLP

(57) ABSTRACT

This disclosure relates compositions comprising upconverting nanocrystals and photoactive compositions and methods using these compositions to modify treat myopia and other ocular conditions. In some cases, the methods use near infrared irradiation to adjust the refractive power of light adjustable ocular lenses. Other methods improve the mechanical strength of the sclera directly.

36 Claims, 5 Drawing Sheets

(56) References Cited

OTHER PUBLICATIONS

Yagci et al., "Photoinitiated Polymerization: Advances, Challenges, and Opportunities", Macromolecules, 2010, 43, 6245-6260.
Zhou et al., "Upconversion nanophosphors for small-animal imaging", Chemical Society Reviews, 2012, 41, 1323-1349.

* cited by examiner

FIG. 2A  FIG. 2B

FIG. 2G
FIG. 2H
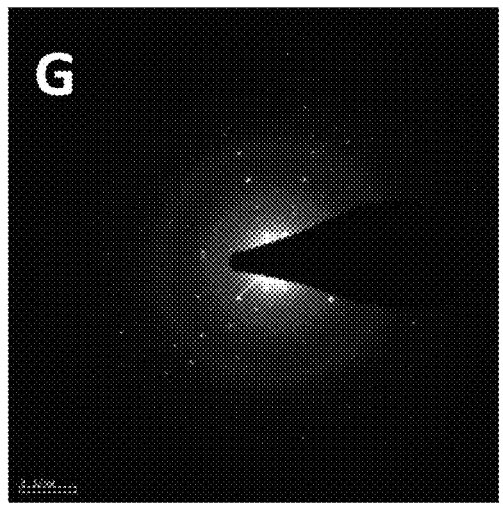
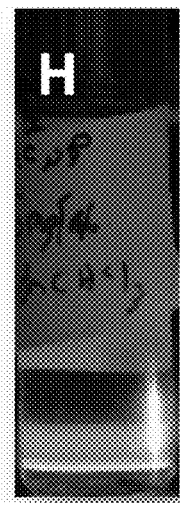
FIG. 3
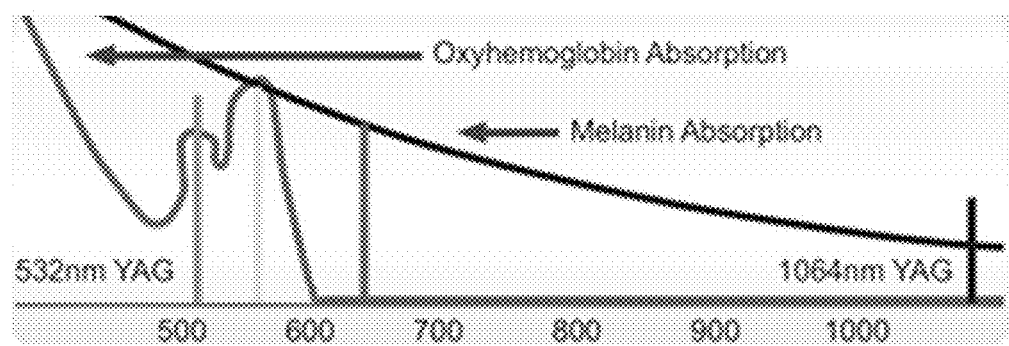

LIGHT ADJUSTABLE INTRAOCULAR LENSES USING UPCONVERTING NANOPARTICLES AND NEAR INFRARED (NIR) LIGHT

CROSS REFERENCE TO RELATED APPLICATIONS

This application claims the benefit of priority to U.S. Application Ser. No. 62/161,415, filed May 14, 2015, the contents of which are incorporated by reference herein in their entirety for all purposes.

TECHNICAL FIELD

This invention relates compositions, including light adjustable lenses, and procedures using these compositions to modify treat myopia and other ocular conditions. In some cases, the methods use near infrared irradiation to adjust the refractive power of light adjustable ocular lenses or to improve the mechanical strength of the sclera directly.

BACKGROUND

Myopia is a rapidly growing problem throughout Asia, particularly in China, Japan, Singapore, and Taiwan, where it is reaching epidemic proportions. Even in the US and some countries in the EU (e.g. Italy), the incidence of myopia is significantly increasing. While most myopia is treatable with refractive correction, some patients with high myopia (>8 diopters) develop degenerative changes in the macula that cause central visual loss. These degenerative changes are not treatable with eyeglasses, contact lenses, or refractive corneal surgery (LASIK). Highly myopic eyes that succumb to degenerative myopia develop progressive scleral thinning and stretching of chorioretinal tissues leading to an outpouching (staphyloma) in the region of the posterior pole. While a staphyloma might develop in the fourth or fifth decade of life, often visual loss occurs 10-20 years later. Indeed, degenerative myopia is the leading cause of visual loss in many Asian countries. At present, there is no effective therapy to retard the progressive ocular axial elongation and scleral thinning that characterize the development of degenerative myopia.

A light adjustable lens (LAL) is an optically transparent optical device whose refractive properties can be changed after its fabrication and insertion into a human eye. Light adjustable lenses (LALs) can have a refraction modulating composition dispersed in a polymer matrix. After the lens has been implanted into the eye and refractive stabilization has occurred, the preexisting optical aberrations or those induced by the surgical procedure are measured. In order to correct these optical aberrations (e.g., spherical power, astigmatism, spherical aberration, etc.), a corresponding amount of UV-Vis radiation is applied to the LAL, which alters the optical properties of the lens either through changes in its shape, its index of refraction, or both. Following one or several irradiations in which portions of the lens have been exposed to selectively and spatially modify the refractive power, the entire lens is irradiated to "lock in" the modified lens.

Prior work describes the use of UV irradiation (320-400 nm) for post-operative power adjustment of LALs. For example, a Helium Cadmium (HeCd) laser operating at 325 nm and a mercury (Hg) arc lamp spectrally filtered for the emission lines at 334 and 365 nm have been used for modifying the refractive power of LALs. Additionally, the prior work also mentions tripled frequency laser diode pumped solid state YAG laser operating at 355 nm, an argon ion laser operating in between 350-360 nm, a deuterium discharge lamp, and broad band xenon:mercury lamps operating with any narrow band spectral filter are useful sources for conducting UV irradiation tests on light adjustable materials and lenses.

However, there are potential safety issues related to each of these sources. Coherent sources (e.g., lasers) are narrowly focused and have high irradiances that can cause permanent damage to retinal tissues. In addition, such sources must be rasterized across the lens requiring complex control of the beam and increased cost. Extended or more diffuse, incoherent sources such as arc lamps offer a more attractive solution from the standpoint of economic (cost and availability) and safety concerns (coherent vs. non-coherent) but they must be attenuated by as much as a factor of 1000 for use in irradiating the light adjustable lenses. Thus, improper use of the lamp, mechanical, or electrical failure could result in applying high irradiances and radiant exposures to the ocular structures causing damage. Taken together, there remains a need in the art for methods to modify the lens so as to increase the achieved power change, reduce the dose required for lock-in, and improve the retinal safety profile of the procedure.

Still further, refractive errors induced by progressive myopia may be corrected by eyeglasses, contact lenses, corneal refractive surgery, or intraocular lenses, but these methods provide only temporary relief and do not prevent visual loss induced by stretching of ocular tissues. Furthermore, current means to treat degenerative myopia are minimally effective. Various attempts have been made to arrest progression of myopia ranging from eyedrops to surgery have either minimal or no proven long term efficacy. Currently, there are no proven means to prevent the excessive ocular enlargement that occurs in degenerative myopia.

Degenerative myopia is often associated with scleral thinning and stretching, the causes of which are not completely understood, but reduction in the mechanical strength of the sclera is a contributory factor. Sufficiently increasing the tensile strength, or modulus, of the sclera would prevent ocular enlargement and reduce progression of myopia. Such a therapy will be useful not only in patients with incipient degenerative myopia, but also in patients with early onset myopia to prevent progression to higher magnitude refractive errors.

Given the limitations of current therapies for treating myopia, new therapies without such limitations are needed. The present invention addresses at least some aspects of this need.

SUMMARY

The present disclosure is directed to compositions, including light adjusting lenses (LALs), and methods of providing and correcting such LALs inserted into an eye of a patient, methods of altering the refractive properties of these LALs, methods for strengthening occular tissue, for example by in situ polymerization or crosslinking of the compositions with the ocular tissue, and the compositions which allow for these methods.

Certain specific embodiments of the present disclosure include photoactive compositions comprising:
 (a) at least one UV-Vis photoinitiator;
 (b) an optional photopolymerizable prepolymer;
 (c) at least one type of upconverting material, preferably an upconverting nanocrystal which, when irradiated by a wavelength of near infrared (NIR) light, emits at least one wavelength of light suitable for activating the UV-Vis photoinitiator.

In certain independent aspects of these embodiment, the optional photopolymerizable prepolymer is present. In other independent aspects of these embodiments, the optional photopolymerizable prepolymer is absent.

In other aspects of these embodiments, the photoactive composition is adapted for use as a light adjustable lens (LAL), preferably an implantable LAL. In certain of these embodiments, the LAL further comprises a separate polymer matrix in which the photopolymerizable prepolymer, the UV-Vis photoinitiator, and the at least one type of upconverting nanocrystal are distributed.

In certain aspects of these embodiments, the photoactive composition or the LAL (or both) further comprises a UV-Vis blocker.

Typical materials used in these photoactive compositions or LALs are described elsewhere in this. Preferably these materials are biocompatible and/or suitable for implantation in a patient, more preferably in a human patient. The photoactive compositions are suitable for implantation or deposition within the eye, and in some cases, certain related compositions (designated "photoactive direct treatment compositions") are deposited directly on the sclera, where they can percolate into the scleral tissue.

In certain embodiments, at least one type of upconverting nanocrystal comprises a lanthanide ion, for example one or more of ion of Er, Gd, Ho, Tm, Y, or Yb. The use of Tm-containing nanocrystals appears to be preferred. Illustrative examples of such upconverting nanocrystal include, but are not limited to, $NaGdF_4$, $NaYF_4$, $BaF_2$, $KYF_4$, or $BaGdF_5$ doped with one or more of Er, Gd, Tm, Y, or Yb. Some specific examples include $NaYF_4$:Yb, Er/Tm; $NaYF_4$:Yb, Er; $NaYF_4$:Yb, Tm; $NaYF_4$:Yb, Er/Gd; $LaF_2$:Yb, Tm. Such upconverting nanocrystal may be of any suitable shape, but hexagonal platelets appear to be preferred. These nanocrystals may also be surface modified with organic moieties to help compatibilize them with the other components of the compositions.

Other embodiments include methods for using and modifying one of the disclosed light adjustable lenses (LALs) or photoactive compositions, which may or may not be implanted into the eye of a patient, by irradiating the LAL or composition with at least one wavelength of near infrared light, wherein the irradiation results in a change in a refractive property of the light adjustable lens or the compositions. This irradiation may be localized in one or more portions of the LAL or composition, or the irradiation may be applied to the entire LAL or composition. In at least some cases, this change in refractive property is the result of partial or complete polymerization, copolymerization, or crosslinking of the pre-polymer materials. Where the LAL further comprises a separate polymer matrix in which the photopolymerizable prepolymer, the UV-Vis photoinitiator, and the upconverting nanocrystal are distributed, the separate polymer matrix may be inert with respect to the polymerization, copolymerization, or crosslinking of the photopolymerizable prepolymer, such that the photopolymerized prepolymer forms pockets or entangled networks of photopolymerized polymer within the separate polymer matrix. In other cases, the materials of the separate polymer matrix may copolymerize or crosslink with the photopolymerizable prepolymer. Depending on the nature of the irradiation and distribution of materials within the LAL or composition, the resulting body may contain localized or distributed networks of polymerized, copolymerized, or crosslinked polymers.

Still other embodiments include methods for using and modifying one of the disclosed compositions to alter at least one mechanical and/or chemical property of a tissue in a patient directly by irradiating one of the disclosed photoactive compositions with near infrared light, wherein the photoactive composition is preferably adjacent to or contacts or has permeated the tissue. In such embodiments, the mechanical and/or chemical property being altered can be tensile strength, compression strength, flexural strength, modulus, elongation, toughness of the tissue, or a combination of two or more of these properties.

In such methods, the tissue is generally an ocular tissue, and may be at least a portion of a cornea and/or a sclera and/or a portion of a lamina cribrosa. In some embodiments, the methods further comprise administering the photoactive composition directly to the tissue of the patient. This may be done either topically or by injection. Where the tissue is an ocular tissue, the photoactive composition may be administered directly to the tissue by retrobulbar injection.

In some embodiments of the methods described herein, the patient has or is at risk of developing an ocular deformation condition comprising one or more of degenerative myopia, regular myopia or scleral staphyloma. For such patients, the methods may be applied to address, either prevent or inhibit further progress of the condition.

BRIEF DESCRIPTION OF THE DRAWINGS

The present application is further understood when read in conjunction with the appended drawings. For the purpose of illustrating the subject matter, there are shown in the drawings exemplary embodiments of the subject matter. However, the presently disclosed subject matter is not limited to the specific methods, devices, and systems disclosed. In addition, the drawings are not necessarily drawn to scale. In the drawings:

FIG. 3 shows absorption spectra for hemoglobin and melanin. Note minimal absorption at 980 nm used to activate one of the disclosed photoactive compositions.

DETAILED DESCRIPTION OF ILLUSTRATIVE EMBODIMENTS

Figure 1:
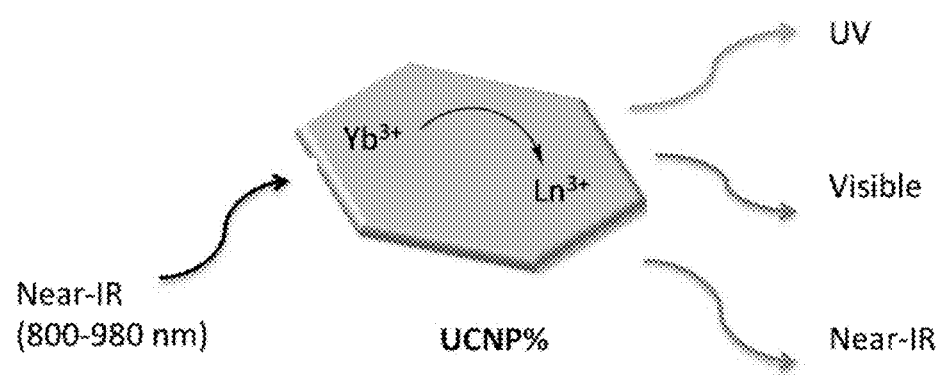
FIG. 1 provides a representation of the operating principles of a lanthanide-doped upconverting nanoparticle (UCNPs) converting near-IR light to higher energy wavelengths that can drive photochemical reactions.
Figure 1:
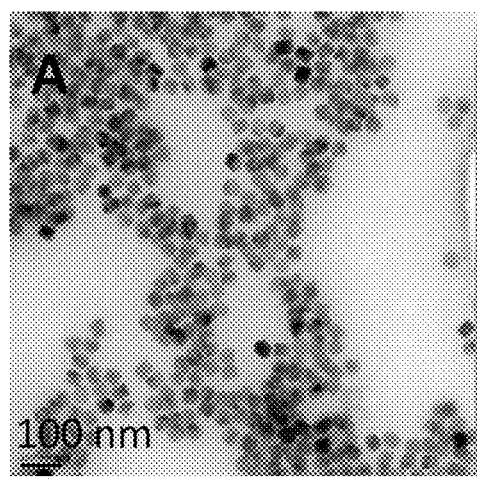
Figure 1:
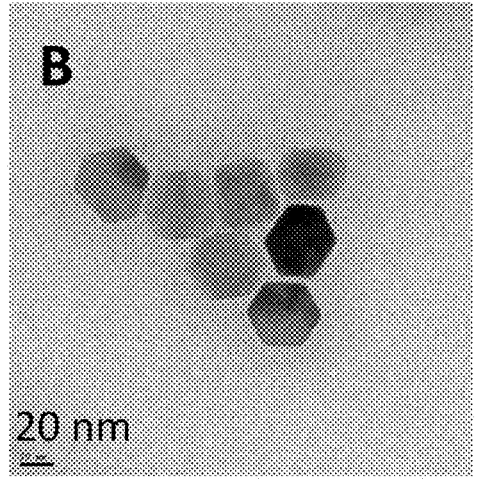
Figure 2C:
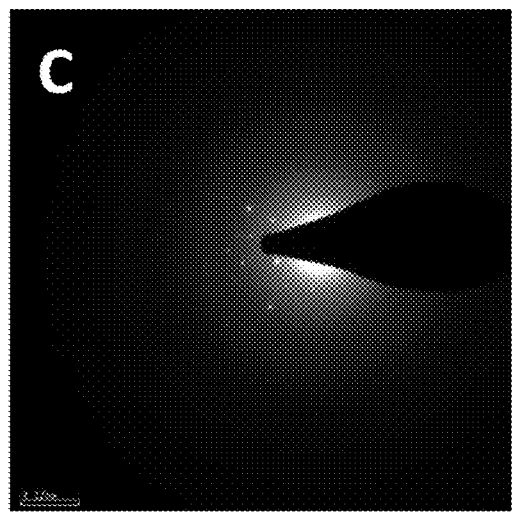
FIG. 2(C) shows the electron diffraction of the nanoparticles.
Figure 2D:
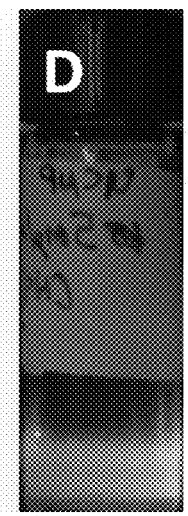
FIG. 2(D) (violet solution) shows photon upconversion for UCNPs of structure $NaYF_4$:Yb/Tm (20/0.2%). Analogous characterization was performed on UCNPs of structure $NaYF_4$:Yb/Er (20/2%)(FIGS. 2(E-G)) denoting tunable photon upconversion (FIG. 2(H), green solution). Sizes of the particles are approximately 30 nm.
Figure 2E:
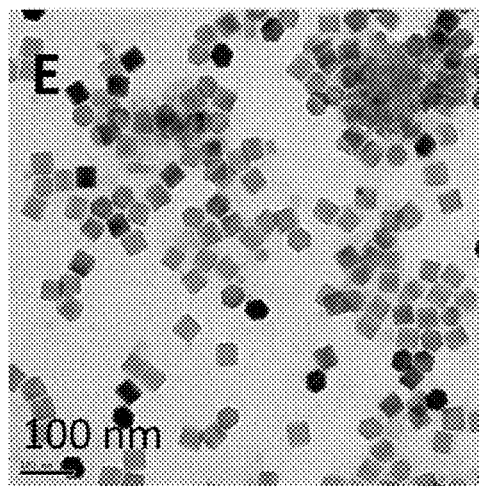
FIGS. 2(A-H) shows analysis of UCNPs and their upconversion using 980 nm light.
FIG. 2(A) shows TEM images showing nanoparticle monodispersity.
FIG. 2(B) shows the size of the particles.
Figure 2F:
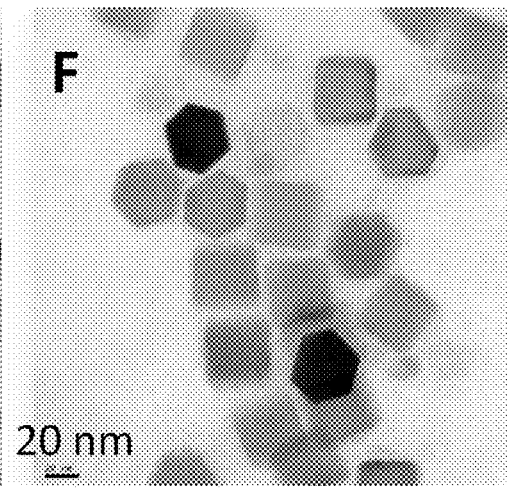

The present disclosure is directed to methods of providing and correcting light adjustable lens (LAL) inserted into an eye of a patient, methods of altering the refractive properties of these LALs, methods for strengthening occular tissue, for example by in situ polymerization or crosslinking of the compositions with the ocular tissue, and the compositions which allow for these methods.

Light offers many distinct advantages over other stimuli for controlling polymerization. The intensity and color can be tuned and used for remote activation of a wide range of materials at a specific time and location with relatively high precision. However, most examples of photo-induced polymerization are limited, as their photochemical reactions require the use of high-energy UV or visible light, neither of which can penetrate deeply into tissues and both of which can cause unwanted damage to surrounding tissues.

An appealing strategy to overcome this problem is the use of near infrared (NIR) light, for example through the use of NIR-absorbing upconverting nanoparticles, to induce the same reactions that are generally catalyzed by UV or visible light. The present disclosure recognizes the potential utility of such an approach in treatment of ocular conditions, including degenerative ocular conditions, for example myopia.

The instant disclosure uses a strategy to harness NIR light that takes advantage of NIR-absorbing nanoparticles, including lanthanide-doped upconverting nanoparticles (UCNPs). Such nanoparticles have the unique luminescent property of converting NIR to shorter wavelength, higher energy radiation (a process described as "upconverting"). Such UCNPs offer many advantages, including low autofluorescence, large anti-Stokes shifts, tunable emissions, and high resistance to photobleaching making them suitable for repetitive imaging. In addition, UCNPs are non-blinking, less light scattering, possess low cytotoxicity and can be activated even in deep tissue, as the NIR used for activation is within the optical transparency window of tissues. Thus, the use of long wavelength photochemistry (e.g., NIR light and UCNPs) appear to provide an ideal platform for the development of a safe and efficient LAL.

The present inventors recognized that the use of upconverting nanoparticles (UCNPs) as the initiator and light-absorbing source in ocular compositions such as LALs, thereby moving the wavelength of irradiation from the near UV to longer wavelengths, would eliminate many of the safety issues associated with adjustment and lock-in for LALs. These systems can be irradiated with >750 nm, or even >900 nm, light and used to carry out photochemistry at lower wavelengths that would be compatible with current LAL technology. As described herein, the concentration must be controlled to a level that allows the photochemistry to take place while shielding the retina. In some embodiments, it is useful to attach the photoinitiator to the nanoparticle to increase the efficiency of the system. UCNPs are easily functionalized on their surface by a variety of photoactive groups. The first advantage of such a system is increased safety since the light is outside of the near UV range.

The use of UCNPs allow the lens to be adjusted and stable without an initial lock-in procedure. The UCNPs require sufficient photon flux to activate and the UV block will prevent the direct activation of the photo initiator (either in solution or attached to the surface of the UCNPs). This combination of features will eliminate two of the issues with the present lens formulations. Since the system will not be activated by ambient light, the lens will not have to be protected between the time it is inserted and locked in. Without a required lock-in, the lens can be adjusted multiple times as needed over a reasonable long period of time. If essential, the lens can eventually be locked-in using a safe beam of >900 nm light. Additional advantages of the system are ease of use by eliminating a lock-in step and eliminating the need for eye protection before lock-in. The system also allows for multiple adjustments over an extended period of time and a safe lock-in if needed.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

Photoactive Compositions

Certain specific embodiments of the present disclosure include photoactive compositions comprising:
(c) at least one UV-Vis photoinitiator;
(d) at least one optional photopolymerizable prepolymer;
(e) at least one type of upconverting material, preferably an upconverting nanocrystal which, when irradiated by a wavelength of near infrared (NIR) light, emits at least one wavelength of light suitable for activating the UV-Vis photoinitiator. In some aspects, these compositions further comprise a UV-Vis blocker. As used herein, "a wavelength of light suitable for activating the UV-Vis photoinitiator" (or similar term) is a wavelength of light in the UV-Vis range, having a higher energy than the irradiating light energy.

In certain independent aspects of these embodiment, the optional photopolymerizable prepolymer is present. In other independent aspects of these embodiments, the optional photopolymerizable prepolymer is absent. These latter compositions—i.e., those absent the optional photopolymerizable prepolymer—are referred to herein as "photoactive direct treatment compositions." In such cases, the photoactive direct treatment composition consists essentially of:
(a) at least one UV-Vis photoinitiator;
(b) an optional UV-Vis blocker; and
(c) at least one type of upconverting materials, preferably an upconverting nanocrystal which, when irradiated by a wavelength of near infrared (NIR) light, emits at least one wavelength of light suitable for activating the UV-Vis photoinitiator, where the special technical feature is the ability of these materials to polymerize or crosslink adjacent materials, for example, one or more compound of a sclera, upon the irradiation by the near infrared (NIR) light.

In other embodiments, the photoactive compostions contain polymeric matrix materials. Such polymeric matrix materials may be useful in defining the structure and properties of LALs. These polymeric matrix materials, described more elsewhere herein, may be inert with respect to polymerization and/or crosslinking, or may contain substituent functional groups capable of such polymerizing, copolymerizing, or crosslinking with like materials, added prepolymers, or other suitably functionalized materials.

Prepolymers

As also described elsewhere herein, the prepolymer may comprise an organic or inorganic monomer, oligomer, macromer, or mixture or combination thereof, capable of polymerization, co-polymerization, and/or crosslinking upon suitable initiation, by activation by at least one UV-Vis photoinitiator. Such prepolymers may contain polymerizable moieties capable of polymerizing, copolymerizing, or crosslinking with other similarly or complementarily functionalized groups. In particular aspects of the invention, the prepolymer may be considered inactive, and in a particular context of the invention is in a non-polymerizable form, until activated by the photoinitiator. Upon its activation, the molecule polymerizes or crosslinks, thereby increasing the modulus and/or strengthening the sclera. In particular embodiments, the polymerization occurs among the monomers and/or with one or more molecules in the scleral tissue, such as collagen, for example. In other particular embodiments, the polymerization comprises polymerization of a monomer around a scleral molecule, such as collagen, glycosaminoglycans, proteoglycans, hyaluronan, dermatan and chondroitin sulphate-based proteoglycans, and the small proteoglycans, decorin and biglycan.

Exemplary polymerizable groups or moieties include functional groups such as alkenyl, allyl, cyclic ether (e.g., epoxy), cyclic acetal, cyclic siloxane, diene, lactone, lactam, vinyl, terminal vinyl ether, vinylidene, N-vinyl carbazole, or [meth]acrylate groups. Other examples of suitable cross-linkable groups include but are not limited to acetoxy, alkoxy, amino, anhydride, aryloxy, carboxy, enoxy, epoxy, halide, isocyano, olefinic, and oxine. Especially useful examples of the photopolymerizable prepolymer include [meth]acrylates, polyhydroxyalkyl [meth]acrylates, [meth] acrylamide], allyloxy, cinnamoyl, styrenes, vinylpyrrolidones, and/or mixtures thereof.

Examples of polymerizable monomers containing a double bond include alkyl, aryl, hydroxyalkyl, cycloalkyl (optionally including an O) or amino acrylates, or alkyl, hydroxyalkyl, cycloalkyl (optionally including an O atom) or amino methacrylates, for example methyl, ethyl, butyl, 2-ethylhexyl, phenyl or 2-hydroxyethyl acrylate, tetrahydrofurfuryl acrylate, isobornyl acrylate, methyl methacrylate, cyclohexyl methacrylate or ethyl methacrylate, hydroxyalkyl acrylates such as 2-hydroxyethyl acrylate, etheralkyl acrylates such as 2-methoxyethyl acrylate, alkoxyor aryloxy-poly(alkylene glycol) acrylates such as methoxypoly (ethylene glycol)acrylates, ethoxypoly(ethylene glycol) acrylates, polyethylene glycol diacrylate, methoxypoly (propylene glycol)acrylates, methoxypoly(ethylene glycol)-poly(propylene glycol)acrylates or their mixtures, aminoalkyl acrylates such as 2-(dimethylamino)ethyl acrylate (DMAEA), fluoroacrylates, silyl acrylates, phosphorus acrylates such as alkylene glycol phosphate acrylates, methacrylic monomers such as methacrylic acid or its salts, alkyl, cycloalkyl, alkenyl or aryl methacrylates, such as methyl methacrylate (MMA), lauryl methacrylate, cyclohexyl methacrylate, allyl methacrylate, phenyl methacrylate or naphthyl methacrylate, hydroxyalkyl methacrylates such as 2-hydroxyethyl methacrylate or 2-hydroxypropyl methacrylate, etheralkyl methacrylates such as 2-ethoxyethyl methacrylate, alkoxy- or aryloxy-poly(alkylene glycol) methacrylates such as methoxypoly(ethylene glycol) methacrylates, ethoxypoly(ethylene glycol)methacrylates, methoxypoly(propylene glycol)methacrylates, methoxypoly (ethylene glycol)-poly(propylene glycol)methacrylates or their mixtures, aminoalkyl methacrylates such as 2-(dimethylamino)ethyl methacrylate (DMAEMA), fluoro methacrylates such as 2,2,2-trifluoroethyl methacrylate, silyl methacrylates such as 3-methacryloylpropyltrimethylsilane, and phosphorus methacrylates such as alkylene glycol phosphate methacrylates, hydroxyethylimidazolidone methacrylate, hydroxyethylimidazolidinone methacrylate, or 2-(2-oxo-1-imidazolidinyl)ethyl methacrylate.

Silicone acrylates may also be used. Further exemplary polymerizable moieties include acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride. Further exemplary polymerizable moieties include: vinylaromatic monomers such as styrene or substituted styrenes, (e.g., alphamethylstyrene), acrylonitrile, acrylamide or substituted acrylamides, 4-acryloylmorpholine, N-methylolacrylamide, methacrylamide or substituted methacrylamides, trimethylolpropane triacrylate, acryloyl chloride, N-methylolmethacrylamide, methacrylamidopropyltrimethyl ammonium chloride (MAPTAC), itaconic acid, maleic acid or its salts, maleic anhydride, alkyl or alkoxy- or aryloxy-poly (alkylene glycol) maleates or hemimaleates, vinyl alcohols, vinylpyridine, vinylpyrrolidinone, (alkoxy) poly(alkylene glycol)vinyl ether or divinyl ether, such as methoxy poly(ethylene glycol)vinyl ether, poly(ethylene glycol)divinyl ether, olefin monomers, among which mention may be made of ethylene, butene, hexene and 1-octene and also fluoro olefin monomers, and vinylidene monomers, among which mention may be made of vinylidene fluoride, these monomers being used alone or as a mixture of at least two aforesaid monomers.

Examples of polymerizable monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

In some embodiments, the photopolymerizable prepolymer comprises a oligomer, macromer, or even polymer having a polyethylene glycol (PEG), a poly[alkyl or dialkyl] siloxane, poly(amino acids), poly(amino acid)-copolymer, polycarbohydrate, a polypeptide/protein, or a polysaccharide backbone.

Exemplary polysaccharides include poly(hyaluronic acid), dermatansulfate, chondroitinsulfate, and/or keratansulfate.

Exemplary polypeptides include elastins. Elastins include native elastin, engineered elastin, or a mixture thereof. Some engineered elastin contain one or more natural amino acid substitutions suitable for polymerization. Alternatively or additionally, the engineered elastin may further or instead comprises one or more non-natural amino acids comprising one or more chemical groups that are appropriate for polymerization, for photoinitiation, or both. For example, an elastin, modified by attachment of two or more methacryl or acryl groups, is a useful material.

Photoinitiators

A photoinitiator, and especially a UV-Vis photoinitiator is a compound capable of converting absorbed light energy, generally or especially UV or visible light, into chemical energy in the form of initiating species, e.g., free radicals or cations.

Based on the mechanism by which initiating radicals are formed, photoinitiators are generally divided into two classes: Type I photoinitiators undergo a unimolecular bond cleavage upon irradiation to yield free radicals; Type II photoinitiators undergo a bimolecular reaction where the excited state of the photoinitiator interacts with a second molecule (a co-initiator) to generate free radicals. UV photoinitiators of both Type I and Type II are known whereas visible light photoinitiators generally belong to the Type II class. Such "initiating species" serve to initiate polymerization in a suitable photopolymerizable material, in this case, either tissue or a photopolymerizable material. The photoinitiators may be in particular embodiments water soluble, inhibited by oxygen, and are preferably biocompatible. Diffusion of the photoinitiators into the sclera and/or other ocular tissue is governed by the size of the compounds, and the hydrophilic and/or hydrophobic interactions of the photoinitiators with the tissue(s).

Any suitable photoinitiator may be used in the invention so long as it is photoactivatable and upon photoactivation it either initiates polymerization of the photopolymerizable prepolymer, functionalized matrix or other component, or directly affects at least one mechanical and/or chemical properties of a desired tissue.

In certain embodiments, the photoinitiator comprises an acetophenone, a benzophenone, a benzoin ether, a benzil ketal, an α-dialkoxyacetophenone, an alkylphenone, an α-hydroxyalkylphenone, an α-aminoalkylphenone, a xanthone, or a thioxanthone moiety.

Exemplary photoinitiators include but are not limited to at least one of an acetophenone, anisoin, an anthraquinone, a sodium salt of anthraquinone-2-sulfonic acid, benzil, benzoin, a benzoin ether (e.g., ethyl, methyl, isopropyl, isobutyl ether), benzophenone, 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, 4,4'-bis(dimethylamino)benzophenone, camphorquinone, 2-chlorothioxanthen-9-one, dibenzosuberenone, 2,2-diethoxyacetophenone, 4,4'-dihydroxybenzophenone, 2,2-dimethoxy-2-phenylacetophenone, 2,2-dimethoxy-1,2-diphenylethan-1-one,4-(dimethylamino)benzophenone, 4,4'-dimethylbenzil, 2,5-dimethylbenzophenone, 3,4-dimethylbenzophenone, eosinY, 4'-ethoxyacetophenone, 2-ethylanthraquinone, fluorescein, hydroxyacetophenone, 3-hydroxybenzophenone, 4-hydroxybenzophenone, 1-hydroxycyclohexyl phenyl ketone, 2-hydroxy-2-methylpropiophenone, 2-mercaptothioxanthone, 2-methylbenzophenone, 3-methylbenzophenone, methybenzoylformate, 2-methyl-4'-(methylthio)-2-morpholinopropiophenone, phenanthrenequinone, 4'-phenoxyacetophenone, or a thioxanthen-9-one. Also useful in the practice of the invention are photoinititators having two initiators linked by a short polymer backbone, e.g., benzoin polydimethyl siloxane Benzoin (B-pdms-B) wherein two benzoin moieties are linked by a dimethyl siloxane bridge. In some cases, the photoinitiator may also be associated with a sensitizer. Suitable sensitizers include p-(dialkylamino aldehyde); n-alkylindolylidene; and bis [p-(dialkyl amino) benzylidene] ketone.

In preferred embodiments, the photoinitiator compound comprises Eosin Y, Eosin B or fluorescein. Eosin Y is most commonly known as a water soluble xanthene dye. Eosin Y is a Type II photoinitiator that is typically used in combination with triethanolamine (TEOA). However, as with other Type II photoinitiators, any suitable co-initiator can be used. Having an absorption peak around 514 nm, Eosin Y is activated efficiently by low-toxicity, visible (green) light. Notably, Eosin Y itself has been shown to exhibit biocompatibility in a range of applications.

Upconverting Materials

Upconverting materials include those materials which exhibit an anti-Stokes shift on absorption and emission of energy; that is, having absorbed a wavelength of energy, it emits one or more wavelengths of higher energy (lower wavelength). In the instant case, these upconverting materials are preferably upconverting nanocrystals which, when irradiated by a wavelength of near infrared (NIR) light, emits at least one wavelength of light suitable for activating the UV-Vis photoinitiator. In certain aspects of this disclosure, the NIR light includes at least one wavelength in range of from about 750 nm to about 1400 nm (or within one of the subranges described elsewhere herein).

Also as described elsewhere herein, such upconverting nanocrystal comprise at least one lanthanide ion. As used herein, the term lanthanide ion refers to an ion of any one of the lanthanide elements, including La, Ce, Pr, Nd, Pm, Sm, Eu, Gd, Tb, Dy, Ho, Er, Tm, Yb, or Lu. In certain preferred embodiments, the lanthanide ion is one or more of Er, Gd, Ho, Tm, Y, or Yb.

Generally, these lanthanide ion dopants are present at levels suitable for its intended purpose, as recognized by a person of skill in the art. In certain specific embodiments, at least one lanthanide ion dopant is present in a range of from about 0.1 to 0.25 mol %, from 0.25 to 0.5 mol %, from 0.5 to 1 mol %, from 1 to 2 mol %, from 2 to 3 mol %, from 3 to 5 mol %, from 5 to 10 mol %, from 10 to 20 mol %, or in a range containing two or more of these ranges.

Given the wavelengths at which these ions typically emit, Tm appears to be preferred, emitting wavelengths well into the lower UV-vis range (e.g., ca. 250-350 nm). In certain embodiments, Tm is present as a dopant at levels in a range of from 0.1 to 3 mol %, preferably from 0.1 to 0.5 mol %, and more preferably at 0.2 to 0.3 mol %.

Such lanthanide ions are typically present as dopants in fluoride or oxide type crystals, for example, in crystals comprising $NaGdF_4$, $NaYF_4$, $BaF_2$, $KYF_4$, or $BaGdF_5$. Compostions of these crystals doped with one or more of Er, Gd, Tm, Y, or Yb are known for their characteristic emissive properties. Specific examples include $NaYF_4$:Yb, Er/Tm; $NaYF_4$:Yb, Er; $NaYF_4$:Yb, Tm; $NaYF_4$:Yb, Er/Gd; and $LaF_2$:Yb, Tm. Other examples include those upconverting nanocrystal comprising $NaYF_4$, $BaF_2$, $CaF_2$, $LaF_2$, $KYF_4$, $Y_2O_3$, $Y_2O_2S$, or $BaGdF_5$ doped with one or more of Er or Tm and Yb (for example, and especially $NaYF_4$:Yb, Er/Tm).

While these nanocrystals are also known to exist in shapes including the cubic, spheroid, and ellipsoid, in preferred embodiments, those upconverting nanocrystal present as hexagonal platelets appear to provide the best results.

These nanocrystals can be surface-modified which to enhance their hydrophilicity or functionality, for example by attaching molecules having two or more linked functional groups, such as amido, amino, carboxylic acid, hydroxy, or thiol group, to their surface. Illustrative molecules used in this capacity include, for example, $C_{2-18}$ carboxy-hydroxy compounds (such as citric or glycolic acid), $C_{2-18}$ dicarboxyacids (such as hexanedioic or 1,10-decanedicarboxylic acid), $C_{2-18}$ carboxy-thiol compounds (such as 11-mercaptoundecanoic acid), $C_{2-18}$ carboxy-amine compounds (such as 6-aminohexanoic acid), $C_{2-18}$ carboxy-thiol compounds (such as thioglycolic acid or 3-mercaptopropionic acid), or $C_{2-18}$ diphosphonates (such as 1-hydroxyethane-1,2-diphosphonic acid). Such molecules may also include oligomers or polymers containing these types of amido, amino, carboxylic acid, hydroxy, or thiol groups. In doing so, the nanocrystals can be made to present one or more of these functional groups external to the nanocrystal surface. See for example, Sedlmeier, A., et al., *Chem Soc. Rev.*, 2015, 44, 1526-1560, which is incorporated by reference for its methods of achieving such surface modifications and the specific modifications achieved. These exposed amido, amino, carboxylic acid, hydroxy, or thiol groups not only modify the hydrophilicity of the particles, improving or affecting their dispersibility in the photoactive compositions, but also provide points of attachment for linking these nanocrystals to the photoinitiators or prepolymers, through complementary functional groups on the latter species, thereby allowing tethering of the upconverting crystal to the photoinitiator, the prepolymer, or both. In certain aspects then, the at least one type of upconverting nanocrystal is tethered to at least one of the photoinitiators by coupling a functional group on the photoinitiator with the presented functional group of the surface modified upconverting nanocrystal.

In typical embodiments, the UCNPs are present in the photoactivated compostions in a range of from about 0.1 to 0.5 wt %, 0.5 to 1 wt %, 1 to 1.5 wt %, 1.5 to 2 wt %, 2 to 2.5 wt %, 2.5 to 3 wt %, 3 to 3.5 wt %, 3.5 to 4 wt %, 4 to 5 wt %, or a combination derived from a combination of tow or more of these ranges, for example, from 0.5 to 1.5 wt %, relative to the weight of the entire photoactive composition.

UV-Vis Blockers

As described elsewhere herein, the present methods are directed to the use of NIR light to activate photoinitiators typically activated by UV-Vis light. While in place, the significant amounts of incident light are absorbed by either melanin or hemoglobin of the tissue in which the compositions are present, preventing activation by these photoinitiators. Nevertheless, in some cases, it is preferred to protect these photoinitiators from ambient light even further. In such cases, the use of additional UV-Vis-blockers is desirable. These UV-Vis-blockers, which may also be characterized as masking or absorbing compounds, are used to absorb or block incident UV-Vis light over a wavelength range that prevents the activation of the UV-Vis photoinitiator with ambient or superambient levels of UV-Visible light. Typically, such UV-Vis-blockers comprise one or more compounds each having extended conjugation. Optionally substituted derivatives of benzotriazole may be used in this capacity.

Light Adjustable Lenses

In some embodiments, the photosensitive compositions described herein are adapted for use as an implantable light adjustable intraocular lens. In some of these cases, in addition to the optional photopolymerizable prepolymer material, the optionally functionalized UV-Vis photoinitiator, and the at least one type of optionally functionalized upconverting nanocrystal, the LAL further comprises a separate polymer matrix material in which the other ingredients are distributed. This separate polymer matrix is a covalently or physically linked structure that may function as a discrete optical element, and typically gives the LAL its shape and effects hardness, flexibility and other physical properties of the LAL. In addition to these characteristics, the LAL is preferably biocompatible, suitable for implantation into the eye of a patient.

The polymer matrix may comprise polymers, homopolymers, and/or copolymers resulting from the polymerization of (meth)acrylates, (meth)acrylamides, phosphazenes, siloxanes, vinyls, or mixtures thereof (or any one or more of the prepolymer materials described elsewhere herein). Illustrative examples of the polymer matrix material include: poly [meth]acrylates such as polyalkyl[meth]acrylates and poly-hydroxyalkyl [meth]acrylates (where alkyl refers to, e.g., methyl, ethyl, or propyl); polyvinyls such as polystyrene and polyvinyl alcohol (PVA); polyvinylpyrrolidone; polyalkylene oxides, polyvinylpyrroles, polyamino acids, polysaccharides, polysiloxanes such as polydimethylsiloxane; polyphosphazenes; polynucleic acids, as well as copolymers thereof. Such polymers may be substituted or unsubstituted, for example by alkyl groups, or any of the functional groups described herein.

In certain embodiments, the matrix polymers or copolymers of the LAL may be inert with respect to crosslinking. In other embodiments, the matrix polymers or copolymers of the LAL contain suitable functional groups capable of crosslinking in the presence of the photoactivation described herein. In either of these embodiments, the LAL may also contain additional photopolymerizable materials, or such additional photopolymerizable materials may be absent. Each of these LAL compositions—polymer matrix materials with or without photoactivatable functional groups, each in the presence or absence of added photopolymerizable prepolymer material—is considered an independent embodiment.

The LAL may also contain one or more other components, each capable of performing one or more functions. For example, in addition to the separate polymer matrix material which provides structure to the LAL, the LAL may also include colorants, anti-reflection compounds, biocompatibility-enhancing agents, antibacterial agents, and the like. Many such colorants, anti-reflection compounds, biocompatibility-enhancing agents, antibacterial agents, etc. are known and are suitable to be included in the matrix material, and may be incorporated according to the desired application.

It is worth noting that one or more of the components in the photosensitive compositions may serve two or more functions attributable to the composition, including polymerizing (copolymerizing), crosslinking, photoactivating, or upconverting through suitable tethering groups (discussed elsewhere)

Methods of Treatment—General Principles

To this point, the disclosure has focused on materials for use in the methods of treatment, but it should be appreciated that the disclosure also includes the methods of using these materials.

In specific aspects of the invention, the methods and compositions may be used for human patients, though the methods may be useful for other mammals, such as a horse, cow, dog, cat, goat, sheep, or pig, for example.

The methods of the present disclosure comprise a step of irradiating a light adjustable lens (LAL) or a photoactive composition with at least one wavelength of near infrared (NIR) light. The duration of the exposure to this NIR light may be of any suitable kind so long as the target molecule(s) are activated from the light. In particular aspects, the light exposure is continuous, although in some cases it is intermittent. The specific duration depends, for example, on the nature of the light source and the concentrations of the ingredients in the LAL and/or photoactive composition. Exemplary light sources for NIR light irradiation include lamps, lasers, and light-emitting diodes (LED). Light is generally used at an intensity of 10-500 mW/cm$^2$ with the particular light intensity dependent on, among other factors, the tissues and photoinitiators compound(s) involved. Individival embodiments include those where the intensity is in a range of from 10 to 50 mW/cm$^2$, from 50 to 100 mW/cm$^2$, from 100 to 200 mW/cm$^2$, from 200 to 300 mW/cm$^2$, from 300 to 400 mW/cm$^2$, from 400 to 500 mW/cm$^2$, from 500 to 750 mW/cm², from 750 to 1000 mW/cm², or a range derived from the combination of two or more of these ranges. One of skill in the art will readily be able to adjust light intensity and time of illumination for a particular application.

Treatments may be repeated in the individual as needed. For example, a second or more treatment may be applied within days of a previous treatment, within weeks of a previous treatment, or within months of a previous treatment.

Specific embodiments include the treatment of a patient having an ocular deformation condition. In specific embodiments, the ocular deformation condition comprises degenerative myopia, regular myopia and/or scleral staphylomas, glaucoma, normal tension glaucoma, and ocular hypertension. In some embodiments, the methods herein may be used prophylactically to reduce the risk of or prevent an ocular deformation condition including any of the foregoing. In other embodiments, the treatments are designed to correct or slow the progression of one or more of these conditions in a patient where the conditions already exist.

In an exemplary procedure, following insertion of the LAL or direct application of the respective photoactive composition, the eye is irradiated with NIR light for a time and under conditions sufficient to effect the desired change, the specific conditions depending on the nature of the treatment and specific composition of the irradiated material. Suitable modes of clinical implementation of irradiation include having the patient in a supine position and delivering light through an operating microscope or having the patient seated and delivering light using a slit lamp system. Because NIR light is used, the light may be delivered through the patient's pupil or other portion of the eye.

In independent embodiments, the directly applied photoactive composition or the LAL may be irradiated entirely or in targeted areas. In separate embodiments, individual portions of the directly applied photoactive compositions may be irradiated separately, either positionally or temporally, or both. Irradiation may involve a patterned application of light. Suitable exemplary methods to control the irradiation pattern incident on the tissue include rastering the irradiation beam, using a spatial light modulator, using a digital mirror device, or using a fiber optic coupled to a laser. The amount of light exposure may also be changed to adjust the degree of polymerization or crosslinking that is occurring in the LAL or tissue. The exposure of the NIR light may directed to a particular region of the sclera or the LAL, as identified by diagnostic imaging. Exemplary diagnostic imaging techniques include ultrasound imaging, optical coherence tomography (OCT) imaging, OCT Doppler imaging, or magnetic resonance imaging (MRI).

Additionally, in separate embodiments, these methods further comprise determining that a change in optical properties is required or desired prior to treatment.

Further, any of these processes may be repeated, after waiting a suitable time to evaluate effect of the change of the properties. In the presence of the UV-Vis blocker, there may be no need to "lock in" the shape or properties, as the presence of the blocker compound will prevent further changes in the LAL until the element is further exposed to the NIR light of the proper frequency and sufficient intensity. This allows for future readjustments at a later time if further corrections are need. Where UV-Vis blocker not present, it may be useful to "lock-in" the shape or properties of the LAL with a more global application of the NIR light.

Methods of Treatment—Irradiating Light Absorbing Lenses (LALs)

Some embodiments provide methods comprising irradiating a light adjustable lens (LAL) with a near infrared wavelength of light, the light adjustable lens comprising the composition of any one of the disclosed compositions described herein, wherein the irradiation of the light adjustable lens results in a change in a refractive property of the light adjustable lens. The LAL may or may not contain a separate photopolymerizable prepolymer, if the matrix material contains suitable functonality to crosslink. In certain of these embodiments, the lens is irradiated either as a whole or in targeted areas. In separate embodiments, individual portions of the LAL may be irradiated separately, either positionally or temporally, or both. The exposure of the NIR light may directed to a region of the LAL identified by diagnostic imaging. Exemplary diagnostic imaging techniques include ultrasound imaging, optical coherence tomography (OCT) imaging, OCT Doppler imaging, or magnetic resonance imaging (MRI).

In specific embodiments, the methods comprise irradiating a light adjustable lens (LAL) with a near infrared wavelength of light, the light adjustable lens comprising:

(a) a photopolymerizable prepolymer material in which is distributed (dispersed or dissolved)

(b) a UV-Vis photoinitiator;

(c) at least one type of upconverting nanocrystal which, when irradiated by a wavelength of light greater than 800 nm, emits at least one wavelength of light suitable for activating the UV-Vis photoinitiator; and (d) optionally a UV-Vis blocker;

wherein the irradiation of the light adjustable lens results in a change in a refractive property of the light adjustable lens. The refractive property may be any property that effects the ability of the LAL to pass light, for example, refractive index, distribution of fluid within the LAL, shape, or local or total density of the material caused by the polymerization or crosslinking of the materials within the LAL.

The composition and characteristics of the various components are described elsewhere, and these compositions and characteristics are equally applicable to these embodied methods. In addition, separate embodiments provide for the compositions which result from the treatment of the LAL with the NIR light; i.e., the compositions comprising a matrix polymer, a partially or completely polymerized prepolymer, and incorporating the upconverting nanocrystal(s).

In separate embodiments, the LAL is implanted in the eye of a patient, and additional embodiments include those steps of implanting the LAL in the eye of a patient prior to irradiation.

Methods of Treatment—Direct Treatments Using the Photoactive Compositions

Methods and compositions for treatment and/or prevention of myopia are presented herein. In particular aspects, the myopia is treated or prevented through strengthening of the sclera, reducing the stretching of the sclera, reducing staphyloma formation, increasing the modulus of the sclera, reducing the compliance of the sclera, and/or reducing the creep in the sclera, for example. In particular, the scleral tissue may be fortified, provide greater mechanical stability to the sclera, and/or prevent further reduction of the strength and/or thickness of scleral tissue by altering its chemical and/or physical structure. This can be accomplished in a number of suitable compositions and methods of use thereof in the invention.

Previously, the present inventors developed a crosslinking strategy to strengthen the posterior pole sclera and prevent staphyloma formation. Eosin Y was applied to the posterior pole sclera followed by irradiation of the treated region with visible light to crosslink scleral collagen and strengthen the eye wall. Because visible light is absorbed by both melanin and hemoglobin (FIG. 3), irradiation of the posterior pole sclera (underlying the macular region) could not be performed though the pupil. Rather, the scleral irradiation was performed under direct observation of the treated region. This means that following application of eosin Y, the posterior sclera was exposed surgically to enable direct irradiation of the exposed tissue with visible light. The invasive nature of this procedure makes it less appealing to patients, especially when used as prophylaxis against future visual loss.

Were scleral crosslinking possible using a longer wavelength of light such as near IR (NIR) light that could readily pass through fundus pigments (melanin, hemoglobin), then irradiation after application of a photoinitiator could be performed through the pupil. This would obviate the need for a surgical procedure to expose the posterior sclera.

The use of NIR light to initiate photochemical processes relies on the use of lanthanide-doped upconverting nanoparticles as conduits to convert NIR to UV and visible wavelengths (FIG. 3). This unique property of UCNPs results from the inner shell configurational electronic transitions within the 4f electrons of lanthanides.[10] The long-lived energy states of lanthanides (i.e., $Y^{3+}$, $Yb^{3+}$, $Er^{3+}$, and $Tm^{3+}$) generates UV and visible light which can be tuned by varying the dopant concentration of lanthanides and host matrix. In principal, the light emitted from UCNPs can be harnessed by photoinitiators that absorb within the chosen wavelengths.

In methods of the present disclosure, involving direct treatment of the tissue, specifically altering one or more mechanical and/or chemical property of a tissue in a patient, the method comprises irradiating any one of the photoactive compositions described herein with near infrared light, wherein the photoactive composition is preferably adjacent to or contacts or has permeated the tissue; wherein the irradiating results in a change in the mechanical and/or chemical property of a tissue in a patient. In a specific subset of these embodiments, the photoactive composition is a photoactive direct treatment composition.

In specific embodiments, the methods comprise irradiating a photoactive composition with near infrared light, wherein the photoactive composition:
  (a) comprises
    (i) a UV-Vis photoinitiator,
    (ii) at least one type of upconverting nanocrystal which when irradiated by the near infrared light, emits at least one wavelength of light suitable for activating the UV-Vis photoinitiator;
    (iii) an optional crosslinking compound;
    (iv) an optional photopolymerizable prepolymer; and
    (v) an optional UV-Vis blocker, and
  (b) is adjacent to or contacts or has permeated the tissue;
wherein
the irradiating results in a change in the mechanical and/or chemical property of a tissue in a patient. The use of the upconverting nanocrystal as a means of initiating polymerization of the photoactive compositions may be viewed as an alternative or improvement to the methods described in U.S. Pat. No. 8,414,911, which issued Apr. 9, 2013, which is incorporated by reference herein for its teaching of materials and methods of treatment.

In these methods, where the composition does not include a separate photopolymerizable compound, upon irradiation, this photoactive composition directly alters a mechanical and/or chemical property of the tissue by causing chemical changes (e.g., crosslinking) of one or more chemical components of the tissue.

In specific embodiments, the tissue is an ocular tissue. In more specific embodiments, the ocular tissue includes at least a portion of a cornea and/or a sclera. In still other embodiments, the ocular tissue includes at least a portion of a lamina cribrosa.

Such treatments are typically provided to patients who have, or are at risk of developing, an ocular deformation condition comprising one or more of degenerative myopia, regular myopia or scleral staphyloma.

In a specific embodiment of the present disclosure, a method of treating and/or preventing myopia in a patient comprises the step of providing to the sclera of the patient a crosslinking compound comprised with a photoinitiator and an upconverting nanocrystal, wherein upon photoactivation of the photoinitiator by the upconverting nanocrystal the crosslinking compound crosslinks at least one molecule of the sclera. The crosslinking compound may be further defined as a single crosslinking molecule or as a chain of crosslinking molecules. The molecule of the sclera may be any molecule comprised at least in part therein, and in specific embodiments is a protein, polysaccharide, carbohydrate, glycosaminoglycan, proteoglycan, or combination thereof. In a specific embodiment, the protein is collagen. In an additional specific embodiment, the crosslinking compound comprises glyceraldehyde.

In these embodiments, the mechanical and/or chemical property being altered by the treatment includes tensile strength, compression strength, flexural strength, modulus, elongation, or toughness of the tissue. The treatment may also result in the strengthening the tissue, stabilizing the tissue shape, changing the shape of the tissue, or a combination thereof.

These methods further comprise administering the photoactive composition, preferably a photoactive direct treatment composition, to the tissue of the patient, either topically (e.g., by eyedrops) or by injection. Each of these modes of administrations is considered an independent embodiment. Where the photoactive composition are administered to the sclera, for example, such administration can be by retrobulbar injection.

The time between delivery of the photoactive composition and irradiation may be adjusted for individual patients and may depend on a variety of factors, including the diffusion rate of the photoactive composition into the target tissue. The photoactive composition may be provided to the individual, and then following an amount of time to ensure that it has reached a particular location and/or sufficient level, for example, the irradiation may then be applied. For example, the photoactive composition may be monitored with slit lamps and/or confocal microscopes while the photoactive composition reaches a certain depth in a particular tissue, and then the photoactive composition is activated with light. In a particular example, the photoactive composition is monitored while it penetrates the cornea to a certain depth, and then the photoactive composition is activated with light. The amount of time between delivery and photoactivation of the photoactive composition may be of any suitable duration.

Wherein the tissue is an ocular tissue, the photoactive composition directly treats or directly reduces the risk of the ocular deformation condition. In related embodiments, the tissue is an ocular tissue and a therapeutically effective amount of the photoactive composition treats a symptom of the ocular deformation condition by strengthening the ocular tissue, stabilizing the ocular tissue shape, changing the shape of the ocular tissue, or a combination thereof.

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of" and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially" of. For those embodiments provided in terms of "consisting essentially of," the basic and novel characteristic(s) is the operability of the methods (or the compositions or devices derived therefrom) as providing a photochemically active compositions activated through the use of one or more upconverting nanocrystals. Materials or steps which do not detract from such operability would be considered within the scope of such embodiments.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Throughout this specification, words are to be afforded their normal meaning, as would be understood by those skilled in the relevant art. However, so as to avoid misunderstanding, the meanings of certain terms will be specifically defined or clarified.

The use of brackets in describing chemical compounds may describe embodiments both where the bracketed content is present or absent, as is understood by the person of skill in the art. For example, the term "[meth]acrylate" refers to independent embodiments of both acrylate and methacrylate. Similarly, the term "[meth]acrylamide" refers to independent embodiments of both acrylamide and methacrylamide The term "biocompatible" as used herein refers to a compound or material that is not toxic or injurious to an individual patient or tissue.

The terms "crosslink" or "crosslinking" carry their normal meaning in its broadest sense, as readily used by a person of skill in the polymer or biochemical arts. It typically refers to formation of a covalent or other bond (e.g., hydrogen bond) between two molecules, typically between two oligomers, macromers, or polymers. For example, a collagen molecule may be crosslinked to other collagen molecules to form a network of interlinked collagen molecules held together by a covalent linkages.

The terms "direct treatment" and "directly treating" and the like refer to the therapies described herein where a photoactive composition, preferably a photoactive direct treatment composition, directly interacts with tissue components to cause a change in the properties of that tissue. Direct treatment with a photoactive composition is distinguished from indirect treatment wherein a photoactive composition interacts with one or more other components of the contacted tissue directly to cause a change in the property of that tissue, for example, directly acting upon a sclera to crosslink the compounds of the sclera, so as to change or alter the properties of that tissue. The terms "direct treatment," "directly treating," "directly reducing the risk of" and the like as used herein additionally refer to the amelioration of at least one symptom of an disease or condition such as an ocular deformation condition. For example, scleral stretching, scleral thinning, or scleral weakening are symptoms of myopia. A skilled artisan recognizes that the treatment does not need to improve vision, such as improving it to its fullest extent. In particular aspects, the terms refer to preventing the progression or slowing the progression of an ocular deformation condition such as degenerative myopia or keratoconous. In a specific embodiment, the vision stabilizes.

The term "mechanical and/or chemical property of a tissue" as used herein refers to a biophysical property of the tissue. Examples of a mechanical property include but are not limited to tensile strength, compression strength, flexural strength, modulus, elongation and toughness (stress-strain). These latter terms confer their normally understood meanings. Examples of a chemical property include but are not limited to the nature of chemical bonds of the tissue components (e.g. collagen versus crosslinked collagen), amount of water of hydration of the tissue is capable of retaining, the biodegradation or turnover rate of tissue constituents.

The term "mechanical stability" as used herein refers to the ability of a tissue or organ to maintain its functional shape even under the influence of stresses imposed on it.

As used herein, "myopia," which may also be referred to as near-sightedness, refers to the ability to clearly see objects up close but not those at a distance. The presently disclosed methods and materials are suitable for addressing all forms and degrees of myopia. In specific embodiments, myopia is pathologic and is diagnosed when eyeball elongation is associated with thinning of ocular tissues in the posterior portion of the globe. High myopia is defined as greater than 8 diopters.

The term "prevention of myopia" as used herein, and described in certain embodiments, refers to the avoidance of the development of myopia. Although in specific embodiments the myopia is permanently avoided, in alternative embodiments the onset of myopia is delayed.

The term "treatment of myopia" as used herein, and described in certain embodiments, refers to the amelioration of at least one symptom of myopia or refers to the retarding of the progression of myopia, for example delaying the progression of scleral stretching, retarding of scleral thinning, or retarding the reducing of scleral strength, for example. The treatment does not need to improve vision, such as improving it to its fullest extent or to normal. In particular aspects, the term refers to preventing the progression or slowing the progression of myopia, such as degenerative myopia, for example. In a specific embodiment, the vision stabilizes.

The terms "nanoparticle(s)" or "nanocrystal(s)" refer to particles or crystals, respectively, having at least one dimension in the range from 1 nm to 100 nm. Such nanomaterials may be shaped as cubes, ellipsoids, platelets, rods, or spheres. In such cases, it is more typical (but not necessarily) that the at least one dimension is characterized as a range of from 1 to 5 nm, from 5 to 10 nm, from 10 to 15 nm, from 15 to 20 nm, from 20 to 25 nm, from 25 to 30 nm, from 30 to 35 nm, from 35 to 40 nm, from 40 to 50 nm, or characterized by a range encompassing two or more of these ranges, for example from 10 nm to 20 nm.

The term "ocular deformation condition" as used herein refers to a disease or physical change in the eye of a patient which results in a change in the dimension of one or more structures of the eye. In some embodiments, this change in dimension causes a change in vision. Specific examples of ocular deformation conditions include degenerative myopia, regular myopia, and scleral staphyloma.

The term "ocular tissue" as used herein refers to a discrete tissue type found in or associated with an eye. In some embodiments, the ocular tissue is a structural tissue which establishes and/or maintains the shape of an eye. In other embodiment, the ocular tissue contributes to the vision of an eye. Specific examples of ocular tissues include the sclera, lamina cribosa, and the cornea.

"Optional" or "optionally" means that the subsequently described circumstance may or may not occur, so that the description includes instances where the circumstance occurs and instances where it does not. Similarly, embodiments which refer to an ingredient or step as being "optionally present," those embodiments include separate independent embodiments in which the step or ingredient is present or absent.

As used herein, the term "photoactive composition" refers to a composition that is activated by the irradiation with near infrared (NIR) light and comprises at least a UV-Vis photoinitiator and an at least one type of upconverting crystal. The term is used to describe independent embodiments where the composition does or does not further contain a photopolymerizable prepolymer. The term "photoactive direct treatment composition" is used to describe a photoactive composition which does not contain any an added photopolymerizable prepolymer material.

The terms "photoinitiator" and especially "UV-Vis photoinitiator" as used herein refer to a compound or a moiety capable of converting absorbed light energy, generally or especially UV or visible light, into chemical energy in the form of initiating species, e.g., free radicals or cations, that activate polymerization or crosslinking of specific functional groups on the polymer precursors.

The terms "photopolymerize" or "photopolymerizable" carries its normal connotations as understood by the person of skill in the art as referring to the ability of a material to be activated by light, in the instant case, by the actions of a photoinitiator and in turn polymerize, copolymerize, or crosslink with other suitable materials. In some embodiments, the photopolymerization comprises polymerization, copolymerization, or crosslinking with another photopolymerizable prepolymers, substituted photoinitiators, functionalized UCNPs, or subunits thereof, polymerization, copolymerization, or crosslinking with a molecule of the sclera, or both. In particular aspects, the term refers to at least one molecule that changes the physical, chemical, or both properties of a tissue such that a tissue modulus is increased and/or such that the strength of a tissue is increased (or that a reduction in strength is prevented or retarded). In the present context, photopolymerizable prepolymers, unless they further contain in-built photoinitiators, do not polymerize in the absence of a suitable chemical initiator; i.e., in the absence of such a photoinitiator, they do not polymerize even in the presence of light.

The terms "polyethylene glycol" and "PEG" as used herein refers to a compound comprising more than one partial or whole poly(ethylene-glycol) backbone monomer of ethylene-glycol with or without differing endgroups and also comprising some or no other monomers such as, for example, dimethyl siloxane, methyl methacrylate, lysine, arginine, chondroitin sulfate, keratin sulfate, etc. In specific embodiments, it is defined as an oligomer or a polymer comprising the repeated units of ethylene glycol (—$OCH_2CH_2$—). Prepolymers described in terms of a particular backbone (e.g., PEG, protein, etc.), where the backbone does not contain a polymerizable moiety or moieties typically contain terminal groups capable of serving this purpose. Exemplary polymerizable moieties are described elsewhere herein.

The term "prepolymer" refers to a compound capable of polymerizing, copolymerizing, or crosslinking with another prepolymer, wherein each prepolymer is similarly or complementarily functionalized to achieve these reactions. In some cases, the prepolymer is a monomer, oligomer, or macromer containing one or more functional groups capable of polymerizing, copolymerizing, or crosslinking with another prepolymer. In some aspects, even macromers or polymers containing suitable functional groups making them suitable for crosslinking with other polymers or with lower monomer, oligomer, macromers, or crosslinking agents ae considered prepolymers. In still other aspects, a photoinitiator (or a UCNP) may contain a functional group capable of participating in polymerization, copolymerization, or crosslinking reactions, in which case the photoinitiator (or UCNP) may be considered to be both the prepolymer and the photoinitiator (or UCNP). In some embodiments, the prepolymer may additionally comprise a crosslinking compound to crosslink, for example, added crosslinkable polymer or with compositions already present within the sclera. Individual crosslinking molecules that are directly active (e.g., glyceraldehydes) or are activated using UV-Vis light are known in the art.

The term "sclera" carries its normal connotation as understood by a person of ordinary skill and refers to the tough, opaque (usually white), outer fibrous coat of the eye, continuous with cornea anteriorly and the optic nerve posteriorly. It comprises collagen and elastic fibers.

"Upconversion" or "upconverting" refers to a property of certain lanthanide nanoparticles to exhibit an anti-Stokes emission, in which lower energy photons are converted to higher energy photons based on long-lived energy states in the inner f-orbitals of certain lanthanide ions. Using NIR light for excitation avoids photodamage of tissue, avoids background fluorescence of biological tissue, and provides for deeper penetration into the tissue.

The term "UV-Visible light" as used herein refers to electromagnetic radiation having a wavelength in a range of from about 200 nm to about 750 nm. Individual embodiments describing UV-Visible light as an important parameter include those in which the range of wavelengths include one or more ranges encompassing 200 to 250 nm, 250 to 300 nm, 300 to 350 nm, 350 to 400 nm, 400 to 450 nm, 450 to 500 nm, 500 to 550 nm, 550 to 600 nm, 600 to 650 nm, 650 to 700 nm, and/or 700 to 750 nm. The term "near infrared light" or "NIR light" refers to electromagnetic radiation in a range of from about 750 nm to about 1400 nm. Individual embodiments describing NIR light as am important parameter include those in which the range of wavelengths include one or more ranges encompassing 750 to 800 nm, 800 to 850 nm, 850 to 900 nm, 900 to 950 nm, 950 to 1000 nm, 1000 to 1050 nm, 1050 to 1100 nm, 1100 to 1200 nm, 1200 to 1300 nm, and/or 1300 to 1400 nm. It should be appreciated that reference to the irradiation by NIR light or by a wavelength of near infrared (NIR) light, as used herein, is intended to connote that the irradiation includes only, or practically only, NIR light; that is, the irradiating light is devoid of any UV-Visible light wavelength capable of activating a UV-Vis photoinitiator, or at least the specific UV-Vis photoinitiator used in the given photoactive composition.

The following listing of embodiments in intended to complement, rather than displace or supersede, the previous descriptions.

Embodiment 1

A photoactive composition comprising:
(e) at least one UV-Vis photoinitiator;
(f) an optional photopolymerizable prepolymer;
(c) at least one type of upconverting material, preferably an upconverting nanocrystal which, when irradiated by a wavelength of near infrared (NIR) light, emits at least one wavelength of light suitable for activating the UV-Vis photoinitiator.

In independent Aspects of this Embodiment, the optional photopolymerizable prepolymer is present. In other independent Aspects of this Embodiments, the optional photopolymerizable prepolymer is absent. The subsequent Embodiments which describe the photopolymerizable prepolymer, unless otherwise indicated, should be read that the photopolymerizable prepolymer is present. Otherwise, the subsequent Embodiments should be read as describing independent embodiments where the photopolymerizable prepolymer is separately both absent and present.

Embodiment 2

The photoactive composition of Embodiment 1, wherein the photopolymerizable prepolymer comprises a polyethylene glycol (PEG), a poly[alkyl or dialkyl]siloxane, a poly[meth]acrylate, a poly(amino acid), a poly(amino acid)-copolymer, a polycarbohydrate, a protein, or a polysaccharide backbone.

Embodiment 3

The photoactive composition of Embodiment 1 or 2, wherein the photopolymerizable prepolymer comprises an acrylate, methacrylate (i.e., [meth]acrylates), acrylamide, methacrylamide (i.e., [meth]acrylamide), allyloxy, cinnamoyl, vinyl, terminal vinyl ether, N-vinyl carbazole, lactone, lactam, cyclic ether (e.g., epoxy), cyclic acetal, cyclic siloxane groups, or a combination thereof. In other Aspects, the photopolymerizable prepolymer may also include a cross-linkable groups such as an acetoxy, alkoxy, amino, anhydride, aryloxy, carboxy, enoxy, epoxy, halide, isocyano, olefinic, or oxine group.

Embodiment 4

The photoactive composition of Embodiment 2, wherein the polysaccharide comprises poly(hyaluronic acid), dermatansulfate, chondroitinsulfate or keratansulfate.

Embodiment 5

The photoactive composition of Embodiment 2, wherein the protein is a native or engineered elastin. Where the elastin is an engineered elastin, it has therefor one or more natural amino acid substitutions suitable for polymerization. Alternatively or additionally, the engineered elastin may further or instead comprises one or more non-natural amino acids comprising one or more chemical groups that are appropriate for polymerization, for photoinitiation, or both]

Embodiment 6

The photoactive composition of any one of Embodiments 1 to 5, wherein the photoinitiator is a Type I or a Type II photoinitiator.

Embodiment 7

The photoactive composition of any one of Embodiments 1 to 6, wherein the photoinitiator comprises an acetophenone, a benzophenone, a benzoin ether, a benzil ketal, an α-dialkoxyacetophenone, an alkylphenone, an α-hydroxyalkylphenone, an α-aminoalkylphenone, a xanthone, or a thioxanthone moiety.

Embodiment 8

The photoactive composition of any one of Embodiments 1 to 7, wherein the photoinitiator comprises at least one of an acetophenone, anisoin, an anthraquinone, a sodium salt of anthraquinone-2-sulfonic acid, benzil, benzoin, a benzoin ether (e.g., ethyl, methyl, isopropyl, isobutyl ether), benzophenone, 3,3',4,4'-benzophenonetetracarboxylic dianhydride, 4-benzoylbiphenyl, 2-benzyl-2-(dimethylamino)-4'- morpholinobutyrophenone, 4,4'-bis(diethylamino) benzophenone, 4,4'-bis(dimethylamino)benzophenone, camphorquinone, 2-chlorothioxanthen-9-one, dibenzosuberenone, 2,2-diethoxyacetophenone, 4,4'-dihydroxybenzophenone, 2,2-dimethoxy-2-phenylacetophenone, 4-(dimethylamino)benzophenone, 4,4'-dimethylbenzil, 2,5-dimethylbenzophenone, 3,4-dimethylbenzophenone, eosinY, 4'-ethoxyacetophenone, 2-ethylanthraquinone, fluorescein, 3'-hydroxyacetophenone, 4'-hydroxyacetophenone, 3-hydroxybenzophenone, 4-hydroxybenzophenone, 1-hydroxycyclohexyl phenyl ketone, 2-hydroxy-2-methylpropiophenone, 2-mercaptothioxanthone, 2-methylbenzophenone, 3-methylbenzophenone, methybenzoylformate, 2-methyl-4'-(methylthio)-2-morpholinopropiophenone, phenanthrenequinone, 4'-phenoxyacetophenone, or a thioxanthen-9-one.

Embodiment 9

The photoactive composition of any one of Embodiments 1 to 8, wherein at least one type of upconverting nanocrystal comprises a lanthanide ion.

Embodiment 10

The photoactive composition of any one of Embodiments 1 to 9, wherein at least one type of upconverting nanocrystal comprises a one or more of ion of Er, Gd, Ho, Tm, Y, or Yb.

Embodiment 11

The photoactive composition of any one of Embodiments 1 to 10, wherein at least one type of upconverting nanocrystal comprises $NaGdF_4$, $NaYF_4$, $BaF_2$, $KYF_4$, or $BaGdF_5$ doped with one or more of Er, Gd, Tm, Y, or Yb.

Embodiment 12

The photoactive composition of any one of Embodiments 1 to 11, wherein at least one type of upconverting nanocrystal comprises $NaYF_4$, $BaF_2$, $CaF_2$, $LaF_2$, $KYF_4$, $Y_2O_3$, $Y_2O_2S$, or $BaGdF_5$ doped with one or more of Er or Tm and Yb ($NaYF_4$:Yb, Er/Tm).

Embodiment 13

The photoactive composition of any one of Embodiments 1 to 12, wherein the at least one type of upconverting nanocrystal is a hexagonal platelet.

Embodiment 14

The photoactive composition of any one of Embodiments 1 to 13, wherein a portion of the at least one type of upconverting nanocrystal is surface modified to present an amino, carboxylic acid, hydroxy, or thiol group, or a combination thereof. In certain Aspects of this Embodiments, the at least one type of upconverting nanocrystal is tethered to at least one of the photoinitiators by coupling a functional group on the photoinitiator with the presented functional group of the surface modified upconverting nanocrystal.

Embodiment 15

The photoactive composition of any one of Embodiments 1 to 14, further comprising a UV-Vis blocker.

Embodiment 16

The photoactive composition of Embodiment 15, wherein the UV-Vis blocker is a benzotriazole compound.

Embodiment 17

The photoactive composition of any one of Embodiments 1 to 16, wherein the composition is adapted for use as or in an implantable light adjustable lens.

Embodiment 18

A method comprising irradiating a light adjustable lens (LAL) with a near infrared wavelength of light, the light adjustable lens comprising the photoactive composition of any one of Embodiments 1 to 17, wherein the irradiation of the light adjustable lens results in a change in a refractive property of the light adjustable lens.

Embodiment 19

A method comprising irradiating a light adjustable lens (LAL) with a near infrared wavelength of light, the light adjustable lens comprising:
(a) a photopolymerizable prepolymer material in which is distributed (dispersed or dissolved)
(b) a UV-Vis photoinitiator;
(c) at least one type of upconverting nanocrystal which, when irradiated by a wavelength of near infrared (NIR) light, emits at least one wavelength of light suitable for activating the UV-Vis photoinitiator; and
(d) optionally a UV-Vis blocker;
wherein the irradiation of the light adjustable lens results in a change in a refractive property of the light adjustable lens.

Embodiment 20

The method of Embodiment 18 or 19, wherein the LAL further comprises a separate polymer matrix in which the photopolymerizable prepolymer material, the UV-Vis photoinitiator, and the at least one type of upconverting nanocrystal are distributed.

Embodiment 21

The method of any one of Embodiments 18 to 20, wherein the LAL is implanted in an eye of a patient prior to irradiation.

Embodiment 22

The method of any one of Embodiments 18 to 21, wherein the refractive property of the light adjustable lens is refractive index, local or total density, shape, or two or more of these parameters.

Embodiment 23

The method of any one of Embodiments 18 to 22, further comprising determining that a change in optical properties is required or desired.

Embodiment 24

A method of altering a mechanical and/or chemical property of a tissue in a patient, the method comprising irradiating a photoactive composition with near infrared light, wherein the photoactive composition:

(a) comprises or consists essentially of a UV-Vis photoinitiator and at least one type of upconverting nanocrystal which when irradiated by a wavelength of near infrared (NIR) light, emits at least one wavelength of light suitable for activating the UV-Vis photoinitiator; and (b) is preferably adjacent to or contacts or has permeated the tissue; wherein the irradiating results in a change in the mechanical and/or chemical property of a tissue in a patient. The photoactive composition may further comprise an optional UV-Vis blocker and an optional crosslinking compound. In certain Aspects of this Embodiment, the photoactive composition further comprises an added photopolymerizable prepolymer. In other Aspects of this Embodiment, the photoactive composition includes any or all of the properties or characteristics described in any one of Embodiments 2 to 16, in the presence of the photopolymerizable prepolymer and/or Embodiments 6 to 16, absent the presence of the photopolymerizable prepolymer.

Embodiment 25

The method of Embodiment 24, wherein the mechanical and/or chemical property is tensile strength, compression strength, flexural strength, modulus, elongation, or toughness of the tissue.

Embodiment 26

The method of Embodiment 24 or 25, wherein the tissue is an ocular tissue.

Embodiment 27

The method of Embodiment 26, wherein the ocular tissue includes at least a portion of a cornea and/or a sclera.

Embodiment 28

The method of Embodiment 26, wherein the ocular tissue includes at least a portion of a lamina cribrosa.

Embodiment 29

The method of any one of Embodiments 24 to 28, wherein the patient has or is at risk of developing an ocular deformation condition comprising one or more of degenerative myopia, regular myopia or scleral staphyloma.

Embodiment 30

The method of any one of Embodiments 24 to 29, wherein the photoinitiator compound comprises any of the photoinitiator compounds disclosed herein.

Embodiment 31

The method of any one of Embodiments 24 to 30, further comprising administering the photoactive composition to the tissue of the patient, either topically or by injection.

Embodiment 32

The method of any one of Embodiments 24 to 31, wherein the tissue is an ocular tissue and the photoactive composition directly treats or directly reduces the risk of the ocular deformation condition.

Embodiment 33

The method of any one of Embodiments 24 to 32, wherein the tissue is an ocular tissue and a therapeutically effective amount of the photoactive composition treats a symptom of the ocular deformation condition by strengthening the ocular tissue, stabilizing the ocular tissue shape, changing the shape of the ocular tissue, or a combination thereof.

Embodiment 34

The method of any one of Embodiments 24 to 33, wherein the exposure to light is directed to a region of the sclera identified by diagnostic imaging.

Embodiment 35

The method of any one of Embodiments 24 to 34, wherein the exposure to light is directed to a region of the sclera identified by ultrasound imaging, optical coherence tomography (OCT) imaging, OCT Doppler imaging, or magnetic resonance imaging (MRI).

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1. Synthesis and Characterization of Upconverting Nanoparticles (UCNPs)

Example 1.1. Procedure for the Synthesis of UCNPs

The following procedure outlines the synthesis of Thulium (Tm) doped Yttrium (Y)/Ytterbium (Yb) upconverting nanoparticles and is general for the synthesis of other co-doped upconverting nanoparticles. It should be appreciated that other lanthanide doped nanoparticles may be prepared by analogous procedures. See, for example, Boyer, J.-C.; Vetrone, F. Cucciam L. A.; Capobianco, J. A. *J. Am. Chem. Soc.* 2006, 128, 7444-7445; and Li, Z.; Zhang, Y. *Nanotechnology* 2008, 19, 345606, which are incorporated herein for their teaching of these materials and methods of preparing such materials.

The lanthanide oxides were first converted to their trifluoroacetate (TFA) salts. To a 3-necked flask equipped with a dean-stark trap was added $Y_2O_3$ (220.2 mg, 0.975 mmol), $Yb_2O_3$ (98.5 mg, 0.25 mmol), and $Tm_2O_3$ (9.6 mg, 0.025 mmol). To this was added 10 mL of a 50% (v/v) solution of trifluoroacetic acid (TFA) in $H_2O$. The reaction mixture was heated to 80° C. and allowed to stir for 30 min until the solution became homogenous. At this point, the reaction temperature was reduced to 50° C. and the mixture allowed to stir under a stream of Argon until complete evaporation of the TFA and water.

The reaction flask was purged with a steady stream of Argon for 10 min. To the reaction mixture was added sodium trifluoroacetate (0.34 g. 2.5 mmol), oleic acid (20 mL) and 1-octadecene (20 mL) under a constant pressure of Argon. The solution was heated to 100° C. for 1 hr until a homogenous suspension was observed. The reaction was slowly heated to 300° C. and maintained at this temperature for 1 hr. The reaction vessel was slowly cooled to room temperature. Ethanol (100 mL) was added and the particles isolated by centrifugation. The particles were washed with ethanol (15 mL), and collected by centrifugation. This was repeated 3 more times to afford a slightly viscous white powder.

Example 1.2. Characterization of the UCNPs

Transmission electron microscopy (TEM) was performed in the Caltech Center for Applied Physics and Materials using an FEI Tecnai F30ST (300 kV) equipped with a high angle annular dark field detector, an Oxford ultra-thin window EDS detector and a Gatan Ultra Scan 1000XP camera.

A small amount of sample (~5 mg) was dispersed in 5 mL of chloroform using sonication to give an approximate 0.1 wt % solution. One drop of the resulting nanoparticle dispersion was dropcasted onto a carbon film supported on a 300 mesh copper grid and allowed to dry in air at room temperature.

Example 2. Procedure for Near-IR Photoinitiated Polymerization

All photocrosslinking studies were performed using an adjustable continuous wave diode infrared laser (Dragon Lasers, M series) operating at 1 Watt. In a typical reaction, 1 mg of oleic acid functionalized nanoparticles (200 microliters of a 5 mg/mL stock solution in chloroform) was charged into a 4 mL scintillation vial. The solvent was removed under a stream of nitrogen. To the residue was added 0.25 mL of a 1:1 Toluene:DMSO mixture that had been degassed. The reaction mixture was sonicated for 2 min to disperse the nanoparticles. To the vial was added 2,2-dimethoxy phenylacetophenone (DMPA, 0.20 mg, 0.001 eq.) 2-hydroxyethyl methacrylate (HEMA 100 mg, 0.768 mmol, 1 eq.) and N,N'-ethylenebis (acrylamide) (290 mg, 1.72 mmol, 2.24 eq.). The contents were briefly agitated and the reaction vial was purged with a stream of argon. The vial was then placed 2 inches from the laser source in a dark room. Photopolymerization under 980 nm light was allowed to occur for 4 hours at which point the mixture had become viscous and solidified upon standing.

Example 3. Observations and Discussion

Successful implementation of the UCNP-mediated polymerization system required the synthesis of lanthanide particles, which was achieved using modifications of established protocols described above (Boyer, J.-C., et al. *J. Am. Chem. Soc.* 2006; and Li, Z. et al. *Nanotechnology*, cited elsewhere herein). As a representative example, particles with diameters of 30 nm consisting of the lanthanides yttrium (Y) co-doped with ytterbium (Yb), erbium (Er) or thulium (Tm) at defined molar ratios (NaYF$_4$; Yb %/Er %/Tm %) could be reproducibly synthesized affording hexagonal-like lattice structures (FIGS. 2(A-H)). This morphology has been determined to have the highest upconversion efficiency among the various lattice substructures that can form. Moreover, it was demonstrated that the nanoparticles were capable of upconversion, as denoted by their emission in the UV and visible range upon exposure to 980 nm light (FIGS. 2(D, H)).

Having established a protocol for the synthesis of UCNPs, their ability to induce free radical polymerization and cross-linking was evaluated. For these initial studies, the monomer 2-hydroxyethyl methacrylate (HEMA), the crosslinking agent N,N'-ethylenebis(acrylamide), and photoinitiator 2,2-dimethoxy-2-phenylacetophenone (DMPA) were chosen. Successful polymerization and crosslinking could be carried out in the presence of 1 wt % of UCNP and 980 nm light operating at 1 W from an infrared diode laser or tunable LED (Table 1, entry 1). Other photoinitiators were explored including benzoin (entry 2), benzoin acetate (entry 3), and eosin Y (entry 4). Still other conditions were explored including varying the light source (entries 1-4, and 5), and conducting the polymerization in the presence or absence of the particles (entries 1-4, and 6). From these studies, polymerization and crosslinking using 980 nm light is dependent on the presence of UCNPs, demonstrating that the upconversion afforded by UCNPs can serve as a practical method for initiating NIR-mediated photochemical polymerization. It is expected that faster kinetics may be achieved by increasing the concentration of the photoinitiator and/or the UCNP, increasing the power of the NIR light source, and/or providing an alternative crosslinkable prepolymer.

TABLE 1

Photoinitiated polymerization and crosslinking using NIR light and UCNPs.

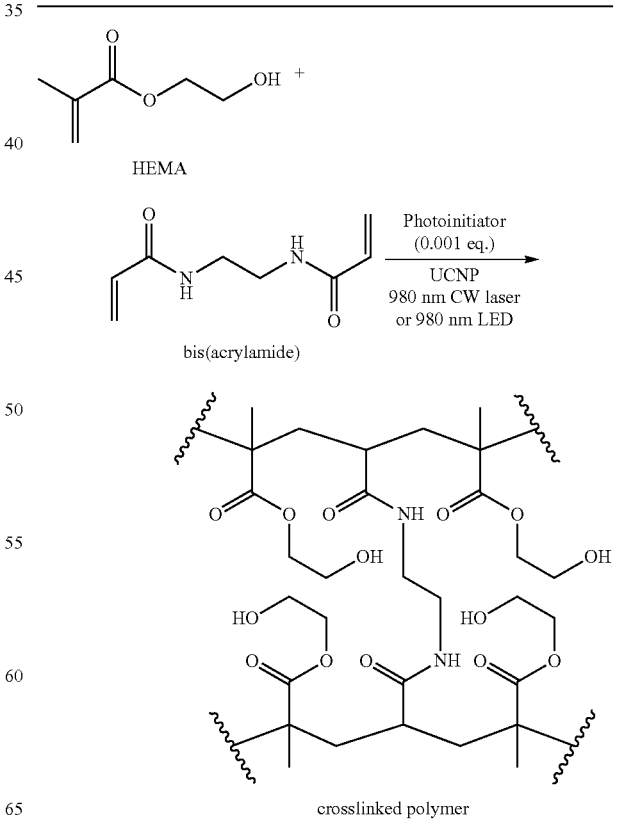

TABLE 1-continued

| Entry | Photoinitiator | Observations |
|---|---|---|
| 1 | DMPA | Photocrosslinking (4 hr) |
| 2 | Benzoin | Photocrosslinking (6 hr) |
| 3 | Benzoin Acetate | Incomplete photocrosslinking (12 hr) |
| 4 | Eosin Y/TEA | Photocrosslinking (8 hr) |
| 5 | No light | No photocrosslinking (12 hr) |
| 6 | None | No photocrosslinking (12 hr) |

Such systems were also capable of polymer crosslinking, albeit with longer exposure times. From these studies, UCNPs were shown to be able to serve as a practical method for initiating NIR-mediated photochemical polymerization and crosslinking. That is, the above observations demonstrated that the UCNPs could be used to initiate polymerization using light having wavelengths in greater than 800 nm light and promote photochemistry that is normally carried out in the near UV, as in current LAL technology.

Figure 4:
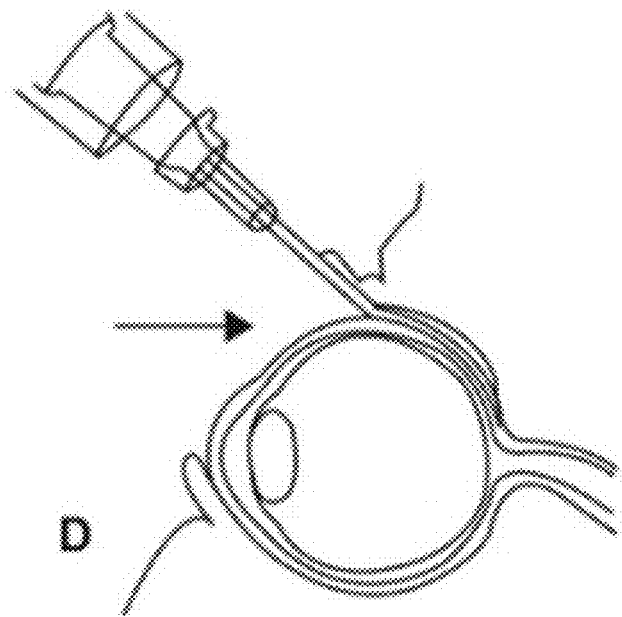
FIG. 4 shows representation of injection of an LAL into region of posterior pole sclera.
Figure 5A:
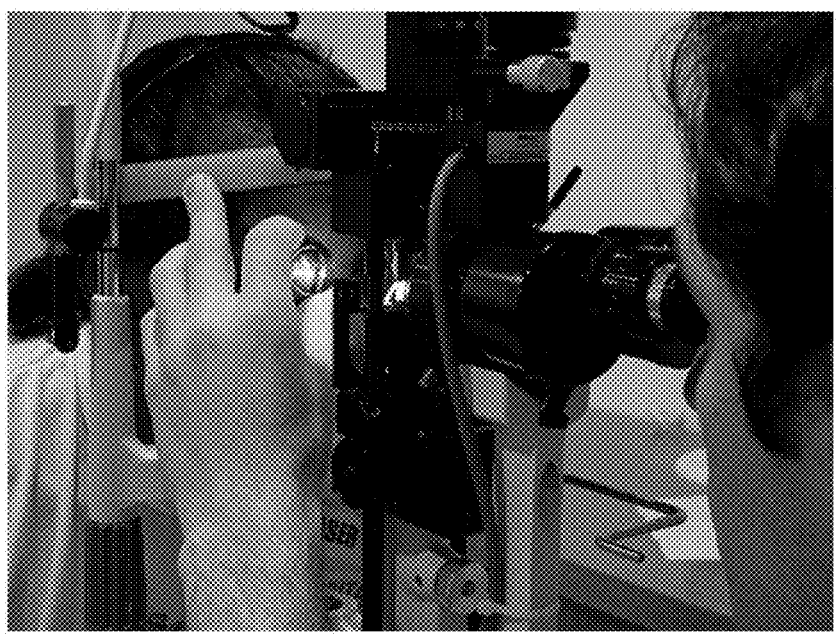
FIG. 5(A) shows illustration of a representative procedure to crosslink an LAL. After adequate diffusion of photoactive direct treatment composition into the posterior pole sclera, irradiation via the pupil is performed to effect sclera crosslinking.
Figure 5B:
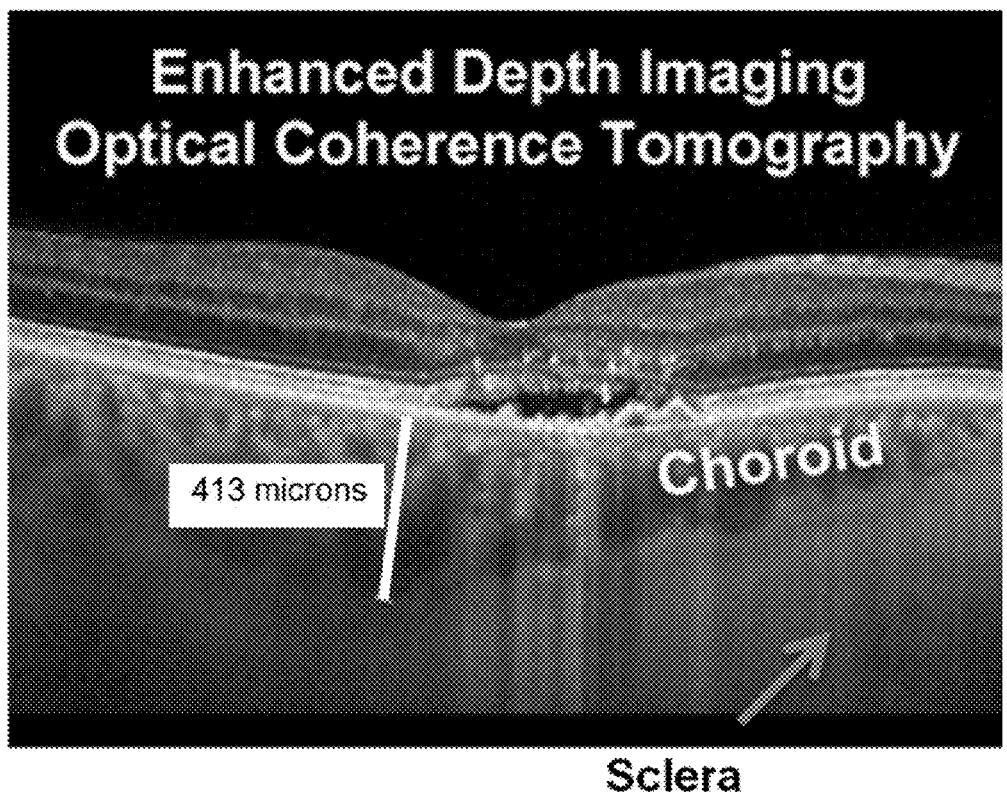
FIG. 5(B) shows representation of the posterior sclera as a target using enhanced depth imaging (optical coherence tomography (OCT)).

The use of upconverting nanoparticles (UCNPs) with attached photoinitiator enabled photo-activation directly through the pupil, because the use of 980 nm light that is not significantly absorbed by either melanin or hemoglobin (FIG. 3). Thus, the UCNP-photoinitiator complex (photoactive composition) would be injected in the retrobulbar space (FIG. 4). After allowing for diffusion of the complex into the sclera, the patient is positioned at the slit lamp for irradiation. The 980 nm light source is focused posterior to the choroid to irradiate the posterior pole sclera with embedded complex (FIG. 5(A)). Resulting release of free radicals effects scleral crosslinking to strengthen the posterior sclera, preventing further thinning and staphyloma progression. The use of optical coherence tomography is incorporated to specifically target the sclera (FIG. 5(B)). Photoactivated dyes, such as described herein, are used to generate the free radicals required for the process.

The unique property of UCNPs to convert NIR to UV and visible wavelengths (FIG. 1) results from the inner shell configurational electronic transitions within the 4f electrons of lanthanides. The long-lived energy states of lanthanides (i.e., $Y^{3+}$, $Yb^{3+}$, $Er^{3+}$, and $Tm^{3+}$) generates UV and visible light which can be tuned by varying the dopant concentration of lanthanides and host matrix. In principal, the light emitted from UCNPs can be harnessed by photoinitiators that absorb within the chosen wavelengths. This tunability of the nanoparticles can be used to test a range of photochemically driven processes and can be optimized for the LAL applications.

The following reference may be useful in understanding the principles of the present disclosure. Each of these is incorporated by reference for their teaching of specific upconverting compounds and methods of making and using the same.

[1] Yagci, Y.; Jockusch, S.; Turro, N. J. *Macromolecules* 2010, 43, 6245-6260
[2] Jacques, S. L. *Phys. Med. Biol.* 2013, 58, R37-R61.
[3] Resch-Genger, U.; Grabolle, M.; Cavaliere-Jaricot S.; Nitschke, R.; Nann, T. *Nat. Methods.* 2008, 5, 763-775.
[4] Li, X.; Zhang, F.; Zhao, D. *Chem. Soc. Rev.* 2015, 44, 1346-1378.
[5] Sun, L.-D.; Dong, H.; Zhang, P.-Z.; Yan, C.-H. *Annu. Rev. Phys. Chem.* 2015, 66, 619-642.
[6] Haase, M.; Schafer, D. *Angew. Chem. Int. Ed.* 2011, 50, 5808-5829.
[7] Bunzli, J. C. G.; Piguet, C. *Chem. Soc. Rev.* 2005, 34, 1048-1077.
[8] Zhou, J.; Liu, Z.; Li, F. *Chem. Soc. Rev.* 2012, 41, 1323-1349.
[9] Wang, F.; Banerjee, D.; Liu, Y.; Chen, X.; Liu, X. *Analyst* 2010, 135, 1839-1854.
[10] Sedlmeier, A.; Gorris, H. H. *Chem. Soc. Rev.* 2015, 44, 1526-1560.
[11] Auzel, F. *Chem. Rev.* 2004, 104, 139-173.
[12] Boyer, J.-C.; Vetrone, F. Cucciam L. A.; Capobianco, J. A. *J. Am. Chem. Soc.* 2006, 128, 7444-7445.
[13] Li, Z.; Zhang, Y. *Nanotechnology* 2008, 19, 3456060
[14] Kramer, K. W.; Biner, D.; Frei, G.; Gudel, H. U.; Hehlen, M. P. Luthi, S. R. *Chem. Mater.* 2004, 16, 1244-1251

As those skilled in the art will appreciate, numerous modifications and variations of the present invention are possible in light of these teachings, and all such are contemplated hereby.

The disclosures of each patent, patent application, and publication cited or described in this document are hereby incorporated herein by reference, each in its entirety, for all purposes.

What is claimed:

1. A composition comprising:
    (a) a photopolymerizable prepolymer in which is distributed;
    (b) a UV-Vis photoinitiator; and
    (c) at least one type of upconverting nanocrystal which, when irradiated by a wavelength of near infrared (NIR) light, emits at least one wavelength of light capable of activating the UV-Vis photoinitiator and photopolymerizing at least a portion of the photopolymerizable prepolymer;
    wherein the composition is sufficiently optically transparent to be used as an intraocular lens.

2. The composition of claim 1, wherein the photopolymerizable prepolymer comprises a polyethylene glycol (PEG), a poly[alkyl or dialkyl]siloxane, a poly[meth]acrylate, a poly(amino acid), a poly(amino acid)-copolymer, a polycarbohydrate, a protein, or a polysaccharide backbone.

3. The composition of claim 1, wherein the photopolymerizable prepolymer comprises an acrylate, methacrylate, acrylamide, methacrylamide, allyloxy, cinnamoyl, or vinyl group.

4. The composition of claim 2, wherein the polysaccharide comprises poly(hyaluronic acid), dermatansulfate, chondroitinsulfate or keratansulfate.

5. The composition of claim 2, wherein the protein is a native or engineered elastin.

6. The composition of claim 1, wherein the photoinitiator is a Type I or a Type II photoinitiator.

7. The composition of claim 1, wherein the photoinitiator comprises an acetophenone, a benzophenone, a benzoin ether, a benzil ketal, an α-dialkoxyacetophenone, an alkylphenone, an α-hydroxyalkylphenone, an α-aminoalkylphenone, a xanthone, or a thioxanthone moiety.

8. The composition of claim 1, wherein the photoinitiator comprises at least one of an acetophenone, anisoin, an anthraquinone, a sodium salt of anthraquinone-2-sulfonic acid, benzil, benzoin, a benzoin ether (e.g., ethyl, methyl, isopropyl, isobutyl ether), benzophenone, 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, 4,4'-bis(dimethylamino)benzophenone, camphorquinone, 2-chlorothioxanthen-9-one, dibenzosuberenone, 2,2-diethoxyacetophenone, 4,4'-dihydroxybenzophenone, 2,2-dimethoxy-2-phenylacetophenone, 4-(dimethylamino)benzophenone, 4,4'-dimethylbenzil, 2,5-dimethylbenzophenone, 3,4-dimethylbenzophenone, eosinY, 4'-ethoxyacetophenone, 2-ethylanthraquinone, fluorescein, 3'-hydroxyacetophenone, 4'-hydroxyacetophenone, 3-hydroxybenzophenone, 4-hydroxybenzophenone, 1-hydroxycyclohexyl phenyl ketone, 2-hydroxy-2-methylpropiophenone, 2-mercaptothioxanthone, 2-methylbenzophenone, 3-methylbenzophenone, methybenzoylformate, 2-methyl-4'-(methylthio)-2-morpholinopropiophenone, phenanthrenequinone, 4'-phenoxyacetophenone, or a thioxanthen-9-one.

9. The composition of claim 1, wherein the at least one type of upconverting nanocrystal comprises a lanthanide ion.

10. The composition of claim 1, wherein the at least one type of upconverting nanocrystal comprises a one or more ion of Er, Gd, Ho, Tm, Y, or Yb.

11. The composition of claim 1, wherein the at least one type of upconverting nanocrystal comprises $NaGdF_4$, $NaYF_4$, $BaF_2$, $KYF_4$, or $BaGdF_5$ each of which is doped with one or more of Er, Gd, Tm, Y, or Yb.

12. The composition of claim 1, wherein the at least one type of upconverting nanocrystal comprises $NaYF_4$, $BaF_2$, $CaF_2$, $LaF_2$, $KYF_4$, $Y_2O_3$, $Y_2O_2S$, or $BaGdF_5$ each of which is doped with one or more of (a) Er or Tm and (b) Yb.

13. The composition of claim 12, wherein the at least one type of upconverting nanocrystal is a hexagonal platelet.

14. The composition of claim 1, wherein a portion of the at least one type of upconverting nanocrystal is surface modified to present an amino, carboxylic acid, hydroxy, or thiol group, or a combination thereof.

15. The composition of claim 1, further comprising a UV-Vis blocker.

16. The composition of claim 15, wherein the UV-Vis blocker is a benzotriazole compound.

17. An implantable light adjustable intraocular lens comprising the composition of claim 1.

18. A method comprising irradiating the light adjustable intraocular lens of claim 17 with a near infrared wavelength of light, wherein the irradiation of the light adjustable intraocular lens results in a change in a refractive property of the light adjustable intraocular lens.

19. The method of claim 18, wherein, the composition of claim 1 further comprises a UV-Vis blocker.

20. The method of claim 18, wherein the light adjustable intraocular lens further comprises a separate polymer matrix in which the photopolymerizable prepolymer material, the UV-Vis photoinitiator, and the at least one type of upconverting nanocrystal are distributed.

21. The method of claim 18, wherein the light adjustable intraocular lens is implanted in an eye of a patient prior to irradiation.

22. The method of claim 18, wherein the refractive property of the light adjustable intraocular lens refractive index, distribution of fluid, shape, or local or total density, or two or more of these properties of the light adjustable intraocular lens.

23. The method of claim 18, further comprising determining that a change in optical properties is required or desired.

24. A method of altering a mechanical and/or chemical property of a tissue in a patient, the method comprising irradiating a photoactive direct treatment composition with near infrared light, wherein the photoactive direct treatment composition:
(a) comprises
(i) the composition of claim 1, in which is further distributed;
(ii) an optional crosslinking compound; and
(iii) an optional UV-Vis blocker,
and
(b) is adjacent to or contacts or has permeated the tissue; wherein
the irradiating results in a change in the mechanical and/or chemical property of a tissue in the patient.

25. The method of claim 24, wherein the mechanical and/or chemical property is tensile strength, compression strength, flexural strength, modulus, elongation, or toughness of the tissue.

26. The method of claim 24, wherein the tissue is an ocular tissue.

27. The method of claim 26, wherein the ocular tissue includes at least a portion of a cornea, a sclera, or both a cornea and a sclera.

28. The method of claim 26, wherein the ocular tissue includes at least a portion of a lamina cribrosa.

29. The method of claim 24, wherein the patient has or is at risk of developing an ocular deformation condition comprising one or more of degenerative myopia, regular myopia or scleral staphyloma.

30. The method of claim 24, wherein the photoinitiator compound comprises an acetophenone, a benzophenone, a benzoin ether, a benzil ketal, an α-dialkoxyacetophenone, an alkylphenone, an α-hydroxyalkylphenone, an α-aminoalkylphenone, a xanthone, or a thioxanthone moiety.

31. The method of claim 24, further comprising administering the photoactive direct treatment composition to the tissue of the patient, either topically or by injection.

32. The method of claim 24, wherein the tissue is an ocular tissue and the photoactive direct treatment composition directly treats or directly reduces the risk of the ocular deformation condition.

33. The method of claim 24, wherein the tissue is an ocular tissue and a therapeutically effective amount of the photoactive direct treatment composition treats a symptom of the ocular deformation condition by strengthening the ocular tissue, stabilizing the ocular tissue shape, changing the shape of the ocular tissue, or a combination thereof.

34. The method of claim 24, wherein the exposure to light is directed to a region of the sclera identified by diagnostic imaging.

35. The method of claim 24, wherein the exposure to light is directed to a region of the sclera identified by ultrasound imaging, optical coherence tomography (OCT) imaging, OCT Doppler imaging, or magnetic resonance imaging (MRI).

36. The implantable light adjustable intraocular lens of claim 17, in which at least a portion of the photopolymerizable prepolymer has been photopolymerized.

* * * * *